(12) United States Patent
Yellin et al.

(10) Patent No.: US 10,849,810 B2
(45) Date of Patent: Dec. 1, 2020

(54) STABILIZATION AND MANIPULATION OF A DELIVERY SYSTEM FOR A PERCUTANEOUS PROCEDURE

(71) Applicant: VALCARE, INC., Newport Beach, CA (US)

(72) Inventors: Nadav Yellin, Ramat Gan (IL); Samuel M. Shaolian, Newport Beach, CA (US); Matan Gedulter, Givat Ella (IL); Boaz Schwarz, Tel Aviv (IL); Tsahi Grimberg, Kfar Saba (IL)

(73) Assignee: VALCARE, INC., Newport Beach, CA (US)

( * ) Notice: Subject to any disclaimer, the term of this patent is extended or adjusted under 35 U.S.C. 154(b) by 652 days.

(21) Appl. No.: 15/661,140

(22) Filed: Jul. 27, 2017

(65) Prior Publication Data
US 2018/0028387 A1 Feb. 1, 2018

Related U.S. Application Data

(60) Provisional application No. 62/367,190, filed on Jul. 27, 2016.

(51) Int. Cl.
*A61G 13/08* (2006.01)
*A61G 13/10* (2006.01)
(Continued)

(52) U.S. Cl.
CPC ............ *A61G 13/101* (2013.01); *A61B 34/70* (2016.02); *A61B 90/50* (2016.02);
(Continued)

(58) Field of Classification Search
CPC ....... A61G 13/101; A61G 13/08; A61G 31/10
(Continued)

(56) References Cited

U.S. PATENT DOCUMENTS 4,953,540 A * 9/1990 Ray et al. .......... A61B 17/0293
600/233
5,609,565 A   3/1997 Nakamura
(Continued)

FOREIGN PATENT DOCUMENTS

EP    2471464 A1   7/2012
GB    1496804 A    1/1978
(Continued)

OTHER PUBLICATIONS

European Search Report for Application EP No. 17 635 256.3 dated Feb. 12, 2020.
(Continued)

*Primary Examiner* — Fredrick C Conley
(74) *Attorney, Agent, or Firm* — Troutman Pepper Hamilton Sanders LLP

(57) ABSTRACT

Disclose herein are embodiments related to a delivery system for performing a minimally invasive procedure, the system including one or more station legs configured to attach to an operating surface and a cross-beam connected to the one or more station legs and running from 0° to 45° relative to a top of the operating surface, wherein a distance between the operating surface and the cross-beam is adjustable. Additionally, an embodiment may have a first arm connected to the cross-beam, a second arm connected to the first arm, and an axial member connected to the second arm, the axial member comprising an axial joint. The delivery system may then be configured to advance to an internal target site using the axial joint while maintaining a stationary trajectory in relation to the internal target site with the delivery system trajectory is modifiable at the target site.

20 Claims, 33 Drawing Sheets

(51) Int. Cl.
  *A61B 34/00* (2016.01)
  *A61B 90/50* (2016.01)
  *A61M 25/01* (2006.01)
  *A61B 90/57* (2016.01)

(52) U.S. Cl.
  CPC ... *A61B 2090/508* (2016.02); *A61B 2090/571* (2016.02); *A61M 25/0113* (2013.01)

(58) Field of Classification Search
  USPC .......................................... 5/626–629, 503.1
  See application file for complete search history.

(56) References Cited

U.S. PATENT DOCUMENTS

| | | |
|---|---|---|
| 2003/0050649 A1 | 3/2003 | Brock et al. |
| 2008/0065011 A1 | 3/2008 | Marchand et al. |
| 2010/0204713 A1 | 8/2010 | Ruiz Morales |
| 2010/0262232 A1 | 10/2010 | Annest |
| 2014/0188130 A1 | 7/2014 | Sanchez et al. |
| 2014/0364939 A1 | 12/2014 | Deshmukh et al. |
| 2015/0073420 A1 | 3/2015 | Bookwalter et al. |
| 2015/0366666 A1 | 12/2015 | Khairkhahan et al. |
| 2016/0100897 A1 | 4/2016 | Avalos et al. |

FOREIGN PATENT DOCUMENTS

| | | |
|---|---|---|
| GB | 2366319 A | 3/2002 |
| WO | 2012038550 A1 | 3/2012 |
| WO | 2015052629 A1 | 4/2015 |
| WO | 2016040526 A1 | 3/2016 |

OTHER PUBLICATIONS

International Search Report and Written Opinion for PCT/US2017/044129 dated Sep. 27, 2017.

European Extended Search Report for EP No. 17860901.2 dated Jun. 5, 2020.

International Search Report and Written Opinion for PCT/US2017/056138 dated Jan. 8, 2018.

\* cited by examiner

STABILIZATION AND MANIPULATION OF A DELIVERY SYSTEM FOR A PERCUTANEOUS PROCEDURE

CROSS-REFERENCED TO RELATED APPLICATIONS

The present application claims benefit of priority under 35 U.S.C. 119(e) to the filing date of U.S. Provisional Patent Application 63/367,190 filed Jul. 27, 2016, entitled, "STABILIZATION AND MANIPULATION OF A DELIVERY SYSTEM FOR A PERCUTANEOUS PROCEDURE," the contents of which is incorporated herein by reference in their entirety.

BACKGROUND

The present disclosure is generally related to a device and method of using a proximal area delivery system.

Generally, percutaneous procedures relate to medical procedures by which internal organs or tissue are accessed via a needle-puncture of the skin rather than by using a more invasive approach by which internal organs or tissue are exposed. A percutaneous approach is typically used in vascular procedures (e.g., angioplasty and stenting). Percutaneous specifically refers to the access modality of a medical procedure, whereby a medical device is introduced into a patient's blood vessel via a needle stick.

Functional mitral and/or tricuspid regurgitation (MR & TR) are the most common type of valve pathologies and are usually associated with mitral valve disease (MVD). Currently, the majority of patients with both MR and TR require surgical treatment, but a large portion of the population does not receive treatment due to the high risk and complexity associated with invasive procedures (e.g., open heart surgery).

Minimally invasive percutaneous treatments are being developed to address this need. The development process is ongoing. However, such processes can be generally characterized as treating structural heart diseases through a catheter to reduce the incidence of open heart surgical intervention. This not only provides a safer and more efficient treatment, but in many cases it is also the only form of treatment available, particularly for high risk patients.

SUMMARY

In an embodiment, a delivery system for minimally invasive procedures includes one or more station legs configured to attach to an operating surface, a cross-beam connected to the one or more station legs and running parallel to a top of the operating surface, a first arm connected to the cross-beam, a second arm connected to the first arm, an axial connected to the second arm, the axial comprising an axial joint. The delivery system is configured to be advanced to an internal target site using the axial joint.

BRIEF DESCRIPTION OF THE DRAWINGS

Aspects, features, benefits and advantages of the embodiments described herein will be apparent with regard to the following description, appended claims, and accompanying drawings where:

DETAILED DESCRIPTION

Figure 1:
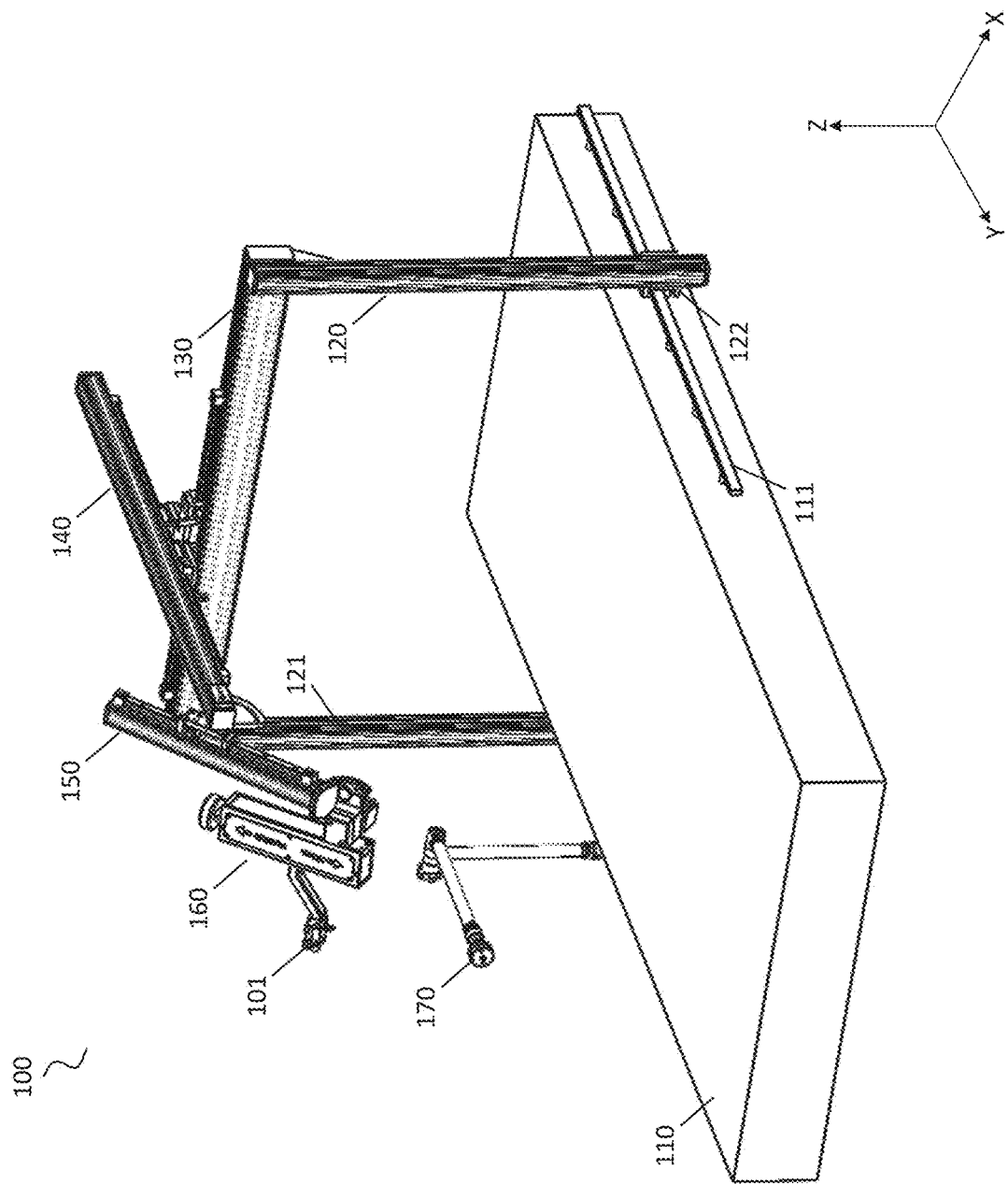
FIG. 1 depicts a perspective view of an illustrative station according to an embodiment.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

As discussed, embodiments herein relate to an accessory device and method that may utilize a rack and rail system with linear and rotational joints to allow for the implementation of a delivery system in a proximal area of the target region (e.g., within one or more heart chambers). An embodiment may provide stabilization, orientation, and fixation of the delivery system within a predefined point or area in space. The delivery system may also have a specific orientation according to the orientation and anatomy of a specific patient.

Thus, an embodiment may include a delivery station for introduction of an implant. A non-limiting specific example may include a semi rigid, D-shaped annuloplasty ring used for treatment of mitral and/or tricuspid regurgitation. In one embodiment, the station may comprise a metal frame composed of several racks, rails, and metal plates. The metal frame may enable manipulation of a distal end of the station to any desired location, while also allowing for precise orientation of the distal end with regard to the target (e.g., the heart).

As would be understood by one skilled in the art, the station may be constructed of various materials and/or material alloys. Moreover, different components of the station may be independently manufactured from different materials and/or material alloys. By way of specific non-limiting example, a station could be constructed of aluminum, stainless steel, polymers, synthetic compounds, semi-synthetic compounds, or any other material that would provide sufficient operational strength. It should be further understood that the joints discussed herein could be comprised of metal and/or polymer components.

Another embodiment may include linear joints that allow translation in the X, Y, or Z axes. The joints may be constructed of sliding bearings with or without rails that are actuated manually or automatically (e.g., motorized automation). Accordingly, the rails may be motorized while also giving a user the ability to manually adjust the rails if desired. In an embodiment, the motorization of the segments may be performed using various techniques (e.g., electrical motors, pneumatic motors, electrical pistons, pneumatic pistons, electromagnets, etc.) or combinations of various techniques.

A further embodiment may include rotational joints. These rotational joints may enable rotation of the distal end of the station around any of the axes (e.g., X, Y, and Z), and thus provide all six degrees of freedom required to be able to bring the distal end of the delivery station to any desired point. This allows a user to align the distal end with any point in space, allowing access to the target site. The delivery system (DS) may be aligned in any desired orientation with respect to the target site as well.

In addition to the wide ranges of motion discussed herein, an embodiment may also have the ability to delicately advance the DS into the target (e.g., within the heart chamber) by use of an axial joint and/or a ball joint. The axial joint may allow advancement and retraction of the DS within the target site in a specific direction of the DS. The ball joint may allow the operator to manipulate the vector of the DS within the target (e.g., heart chamber).

The illustrated example embodiment will be best understood by reference to the figures. The following description is intended only by way of example, and simply illustrates certain example embodiments.

Figure 23:
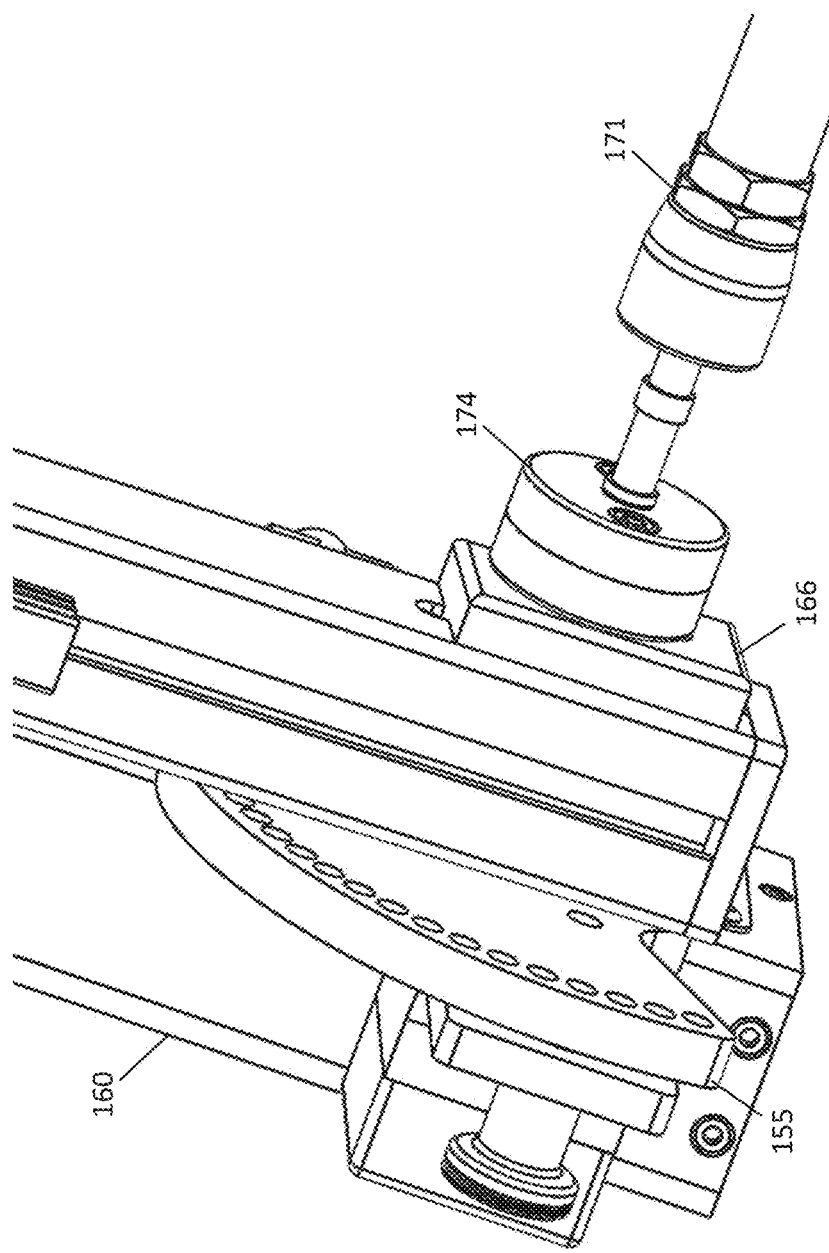
FIG. 23 depicts a view of an illustrative connection between a support arm and an axial member according to an embodiment.
Figure 24:
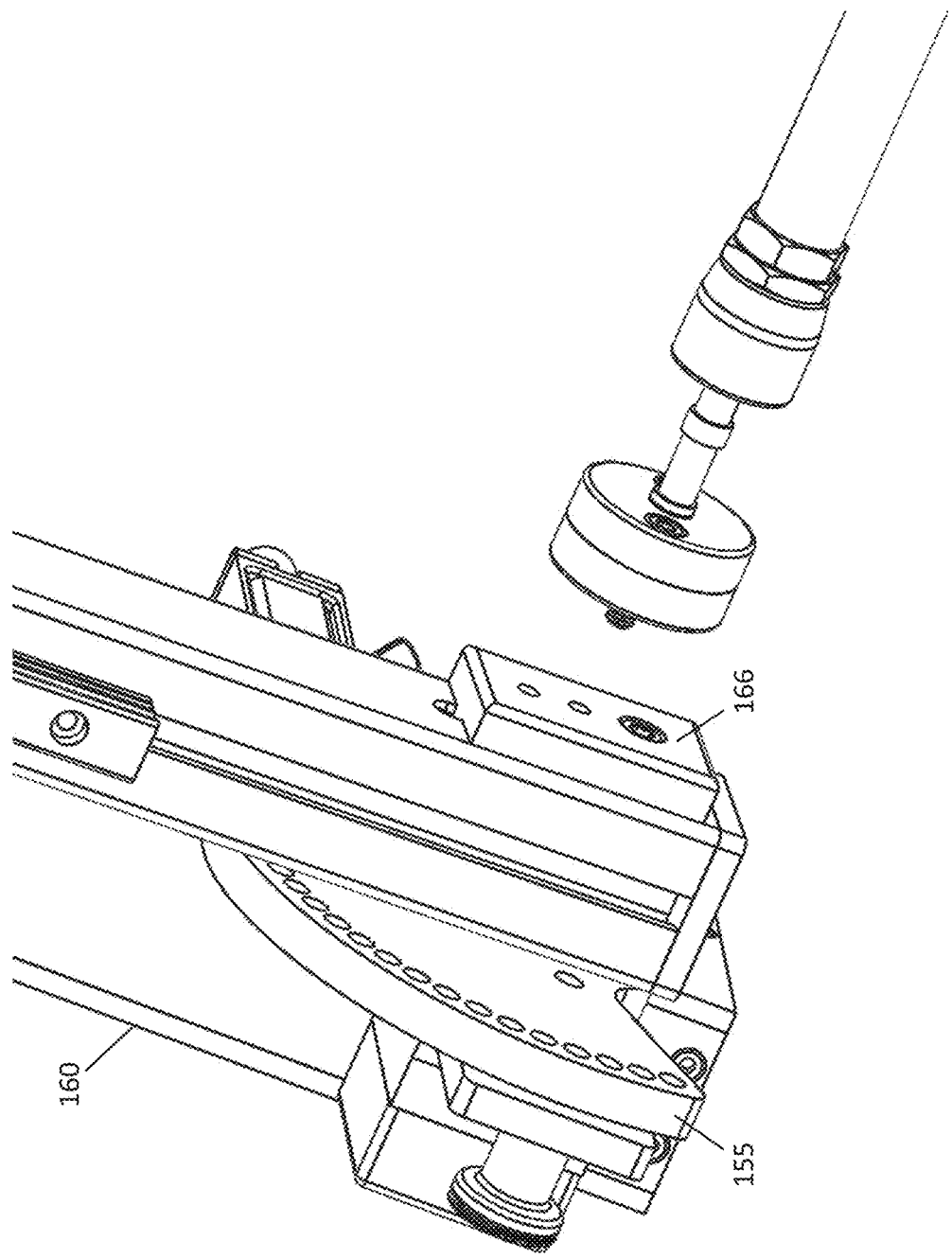
FIG. 24 depicts a view of another illustrative connection between a support arm and an axial member according to an embodiment.

FIG. 1 shows a perspective view of an illustrative station 100. In one embodiment, the station 100 may comprise a distal end 101, an operating room bed 110, operating room bed rail 111, station legs 120 and 121, one or more connecting blocks 122, a station cross beam 130, a long (e.g., 1000 mm) station arm 140, a short (e.g., 500 mm) station arm 150, an axial member 160, and a support arm 170. The station legs 120 and 121 may be arranged in the z-axis of the station 100 to allow the station to connect to the operating room bed via one or more connecting blocks, such as 122. In one embodiment, the axial member 160 helps impart inferior and superior movement within the target site (e.g., the heart) as well as y-axis rotation. Additionally, in another embodiment, the support arm 170 may provide stability as shown in FIGS. 23-24.

The station 100, as discussed, may be made using various materials. For simplicity the station 100 or frame may be referred to herein as metal. However, it should be understood by those skilled in the art that this language is only for simplicity of explanation purposes, and, as discussed, the station 100 may be manufactured out of various materials and various combinations of materials. Thus, an embodiment may have a metal frame in combination with translational and rotational joints that allow the delivery system to be controlled and positioned to a desired location with a desired orientation. Using the joints, an embodiment may move and relocate the distal end 101 of the system in any X, Y, and Z coordinate plane in order to access the desired area of the patient (e.g., the patient's chest), and position the distal end 101 in any vector, specifically towards the intended target (e.g., the mitral valve from the X, Y, and Z coordinate). An embodiment, may also allow translation in the X, Y, and Z directions along linear lines as well as rotation of the attachment point around the X, Y, and Z axes (e.g., like a ball joint).

In one embodiment, the attachment of the station legs 120 and 121 to an operating room or catheterization laboratory bed 110 may be done via operating room bed rails 111. The operating room bed rails 111 may be permanently attached to the operating room bed 110 or interchangeable. In one embodiment, movement of the distal end 101 in the z-axis may be from about 200 mm to about 900 mm above the operating room bed 110.

In one embodiment, the station 100 may be used in a sterile field and be used as a sterilized unit after sterilization (e.g., in an autoclave or using the ethylene oxide (ETO) process). Additionally or alternatively, different individual components may be draped on or around the system in order to maintain sterility while other components can be sterilized according to the operator's requirements.

Figure 2:
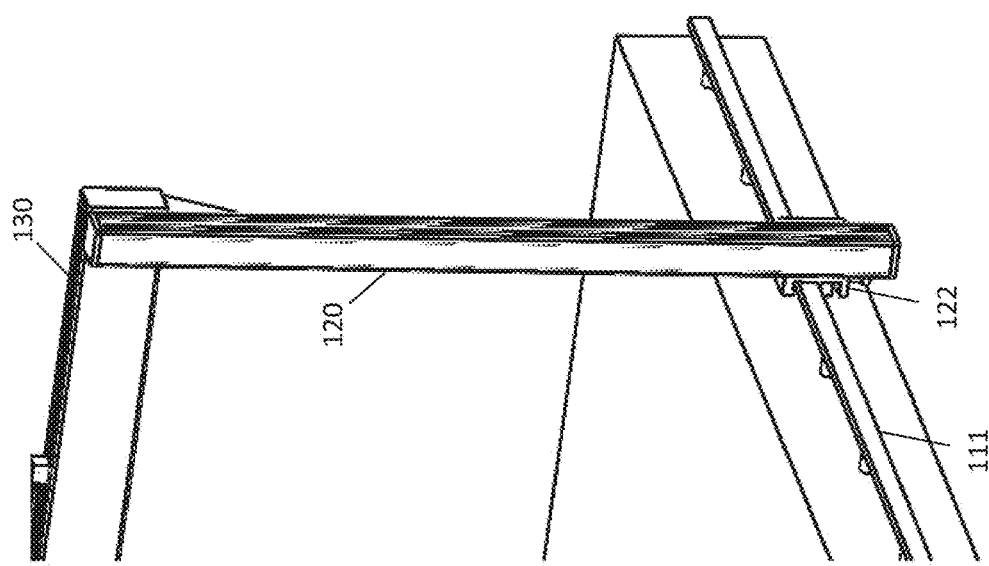
FIG. 2 depicts an illustrative view of a connection of the station to an operating room bed according to an embodiment.

Referring to FIG. 2, an illustrative connection of the station 100 to the operating room bed is illustrated. In one embodiment, the example connection may include a station cross beam 130, station legs 120 or 121, a connecting block 122, and an operating room bed rail 111. In the depicted embodiment, the station legs 120 or 121 are attached via a connecting block 122. As shown in FIG. 2, a station leg 120 (or, alternatively, 121) may connect to an operating bed 110 using the connecting block 122 via a bed rail 111. Thus, in one embodiment, a connecting block 122 may be used to fasten a station leg 120 to the operating bed.

Figure 3:
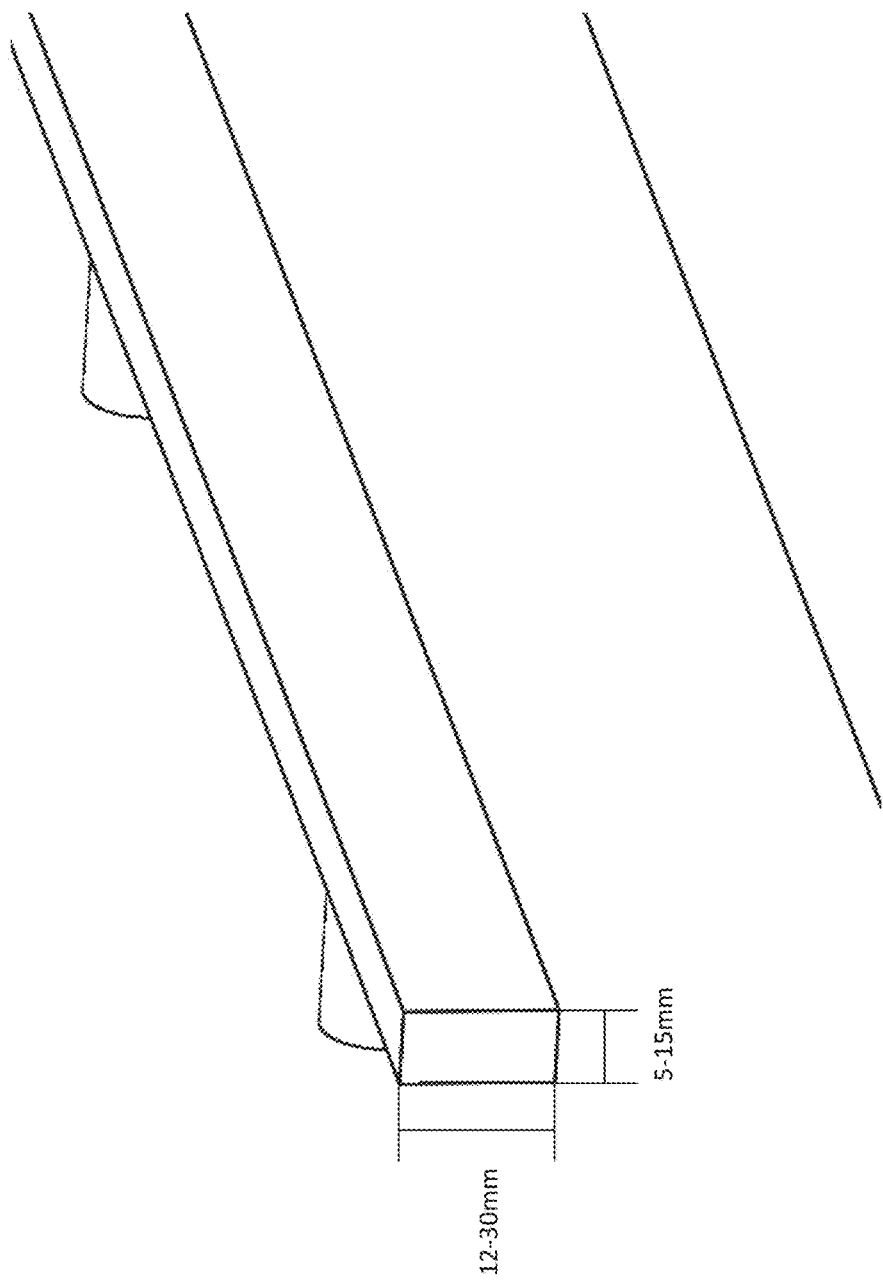
FIG. 3 depicts a detail view of an illustrative bed rail according to an embodiment.
Figure 4:
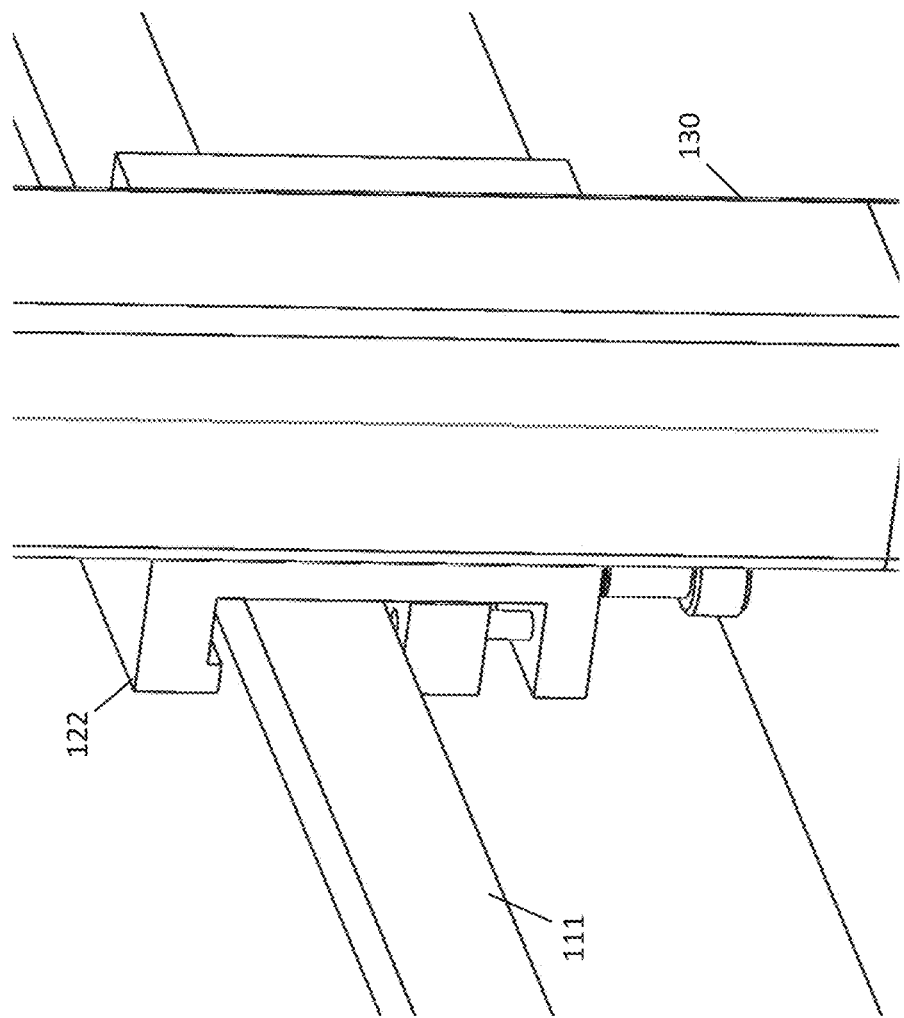
FIG. 4 depicts a detail view of an illustrative station leg, connecting block, and bed rail according to an embodiment.

Further detail regarding the operating room bed rail 111 is shown in FIG. 3. In one embodiment, and as shown in FIG. 3, the width of the operating room bed rail 111 may be in a range of about 5 mm to about 15 mm, and the height of the operating room bed rail 111 may be in a range of about 12 mm to about 30 mm. Referring now to FIG. 4, an enlarged illustration of an illustrative connecting block 122 is shown. In one embodiment, as shown in FIG. 4, the connecting block 122 may be attached to a station leg 120 using one or more screws 124 (see FIG. 5) and may be attached to the operating room bed rail 111 using a clamp system that adjusts to fit a variety of bed rail sizes, as discussed herein and shown in FIG. 3.

Figure 5:
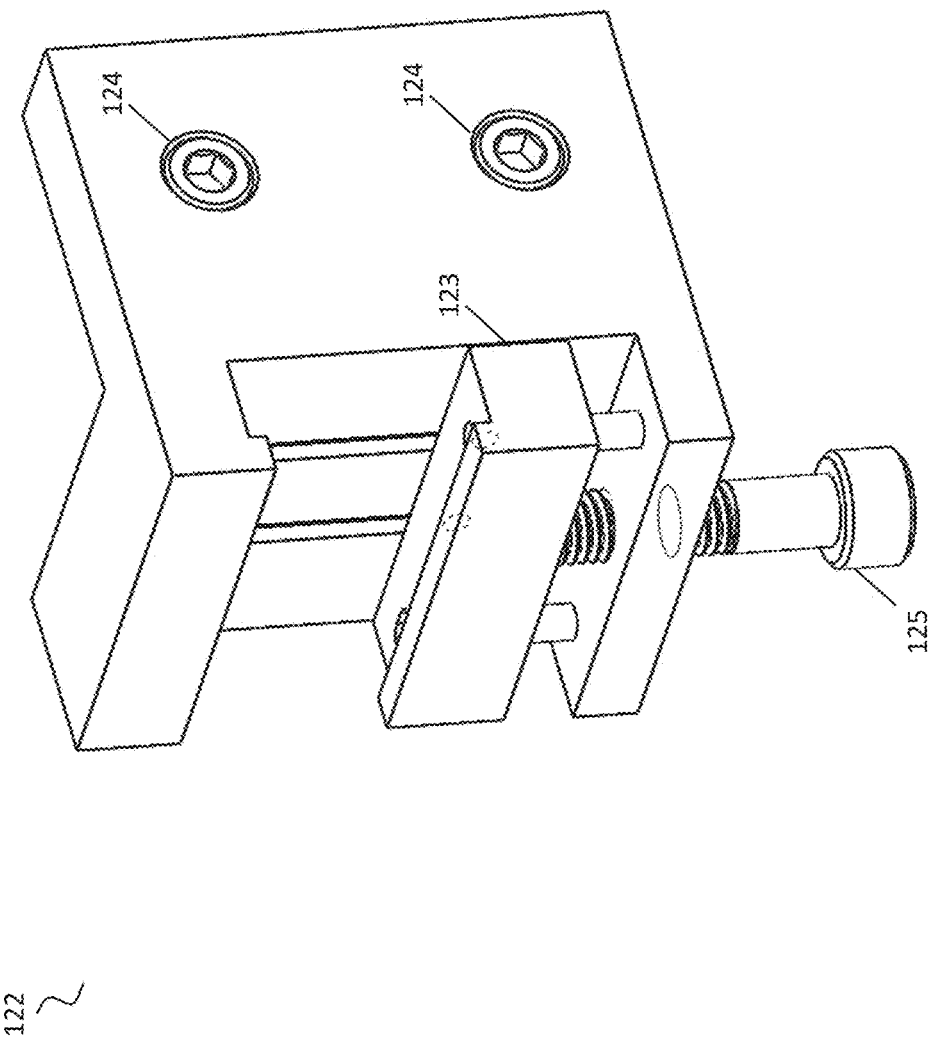
FIG. 5 depicts a detail view of an illustrative connecting block according to an embodiment.

As shown in FIG. 5, a connecting block 122 may include a tightening block 123, one or more screws 124, and a threaded device 125. The tightening block 123 may be tightened or closed to secure the connection between a station leg 120 (or, alternatively, 121) and 121 and an operating room bed rail 111. In one embodiment, the connecting block 122 may use, for example, a threaded device 125. When the connecting block 122 is closed, an embodiment may lock the leg 120 into a particular position with minimal to no relative movement between the leg(s) and the rail 111 or bed 110.

Securing alignment of the station 100 in the z-axis may be performed using an attachment mechanism to connect a station leg 120 to a connecting block 122 (e.g., via screws 124 (FIG. 5) or other fastening hardware). Additionally or alternatively, an embodiment may attach via a rail system with a continuous or discrete lock. This may allow for a more refined alignment of the z-axis using the connection block 122.

Figure 6:
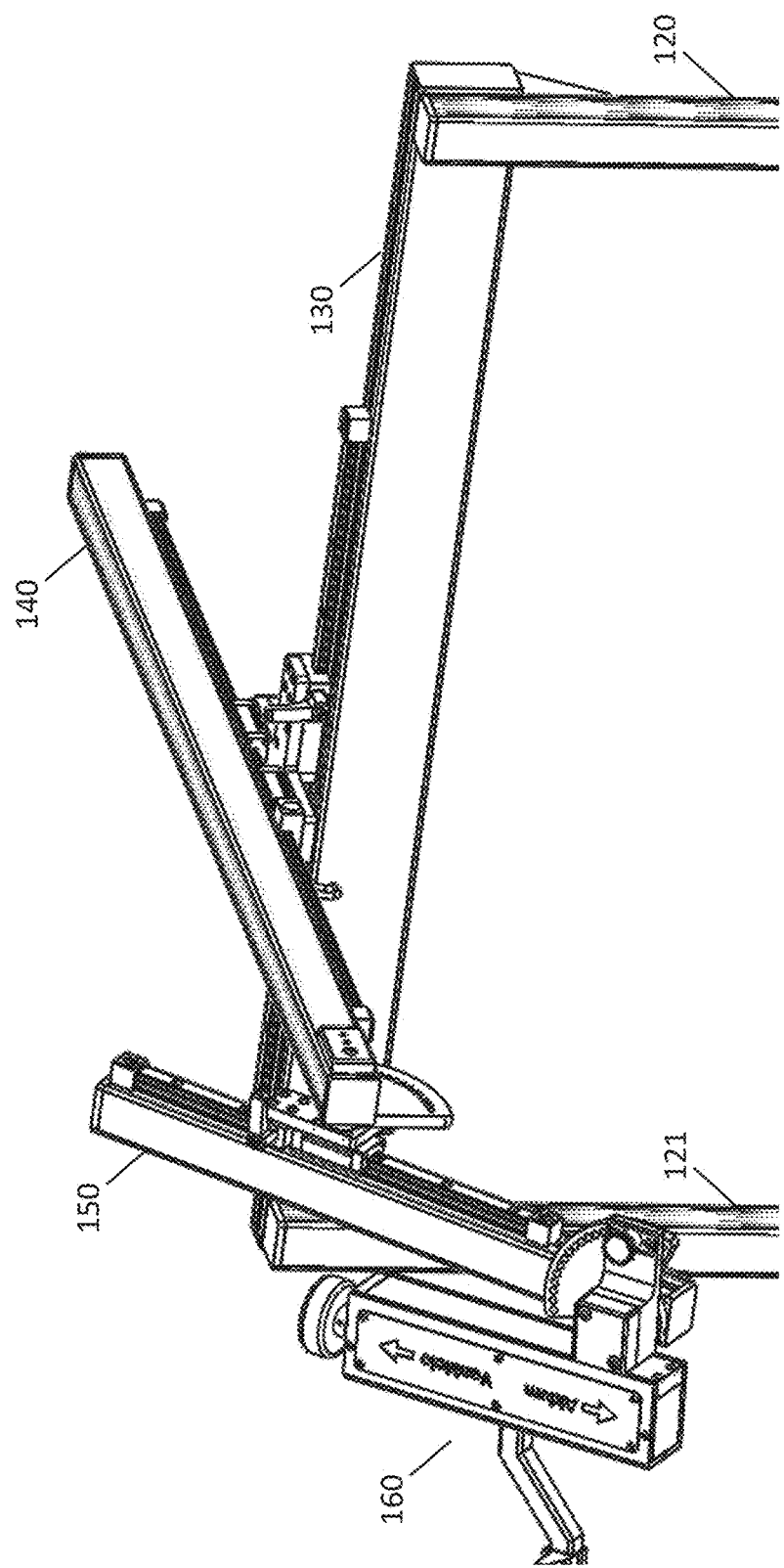
FIG. 6 depicts a perspective view of an illustrative cross beam and arm connection according to an embodiment.

Referring now to FIG. 6, an illustrative station cross beam 130 and arms 140 and 150 are shown. In one embodiment, the station cross beam 130 and arms 140 and 150 may include a right station leg 120, a left station leg 121, a station cross beam 130, a long (e.g., 1000 mm) station arm 140, a short (e.g., 500 mm) station arm 150, and an axial member 160. In one embodiment, the right station leg 120 and left station leg 121 may be in the z-axis of the station 100, and the station cross beam 130 may be in the x-axis of the station. As discussed herein, in an embodiment, a long station arm 140 may be located in the y-axis of the system, and a short station arm 150 may have y-axis and x-axis rotation. Additionally, an axial member 160 may have inferior and superior movement within the target site (e.g., the heart) and a rotational axis around the y-axis.

Figure 7:
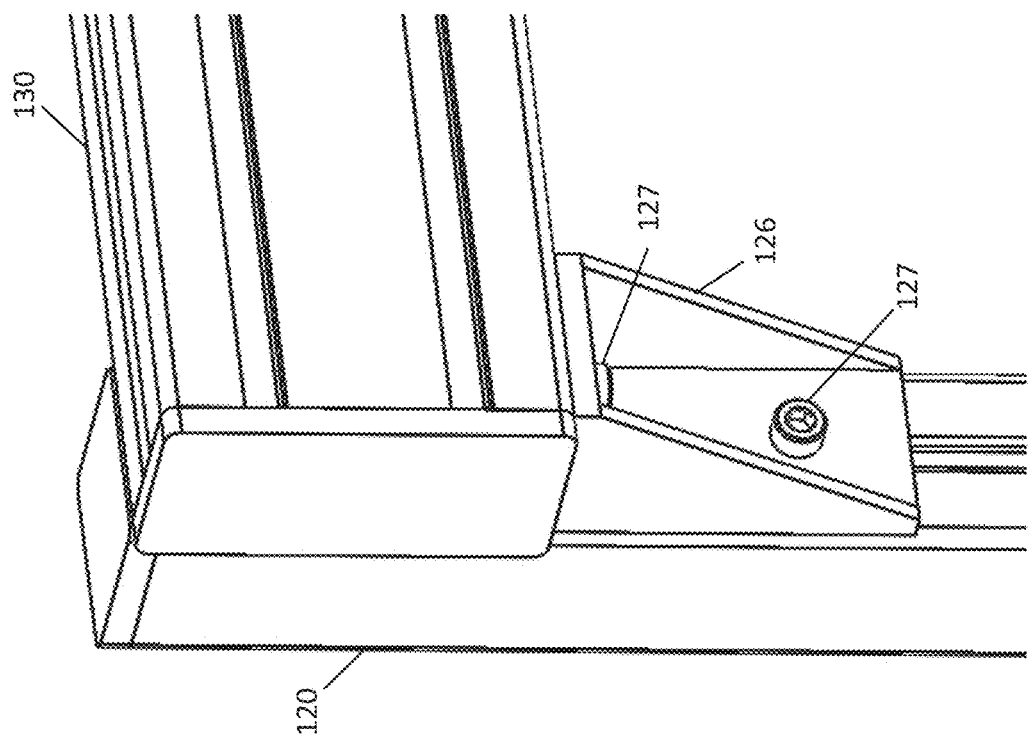
FIG. 7 depicts a detail view of an illustrative cross beam and station leg connection according to an embodiment.

Referring to FIG. 7, an illustrative connection between a station cross beam 130 and a station leg 120 is shown. In one embodiment, the attachment of the station cross beam 130 to the station leg 120 may be via a 90 degree plate 126, where the plate may be made of various materials (e.g., a metal, stainless steel, aluminum, etc.) that attach the station leg to the station cross beam via screws 127 and 127. Additionally or alternatively, this connection (i.e., the connection between the station cross beam 130 and the station leg 120 may be formed using a rail system with a discrete or continuous locking mechanism(s) to allow for smooth movement. In a further embodiment, the movement of the connection may be performed using various techniques (e.g., electrical motors, pneumatic motors, electrical pistons, pneumatic pistons, electromagnets, etc.) or a combination of the various techniques. This electro/mechanical movement allows control over the movement of the station cross beam 130 in the z-axis of the system.

Figure 8:
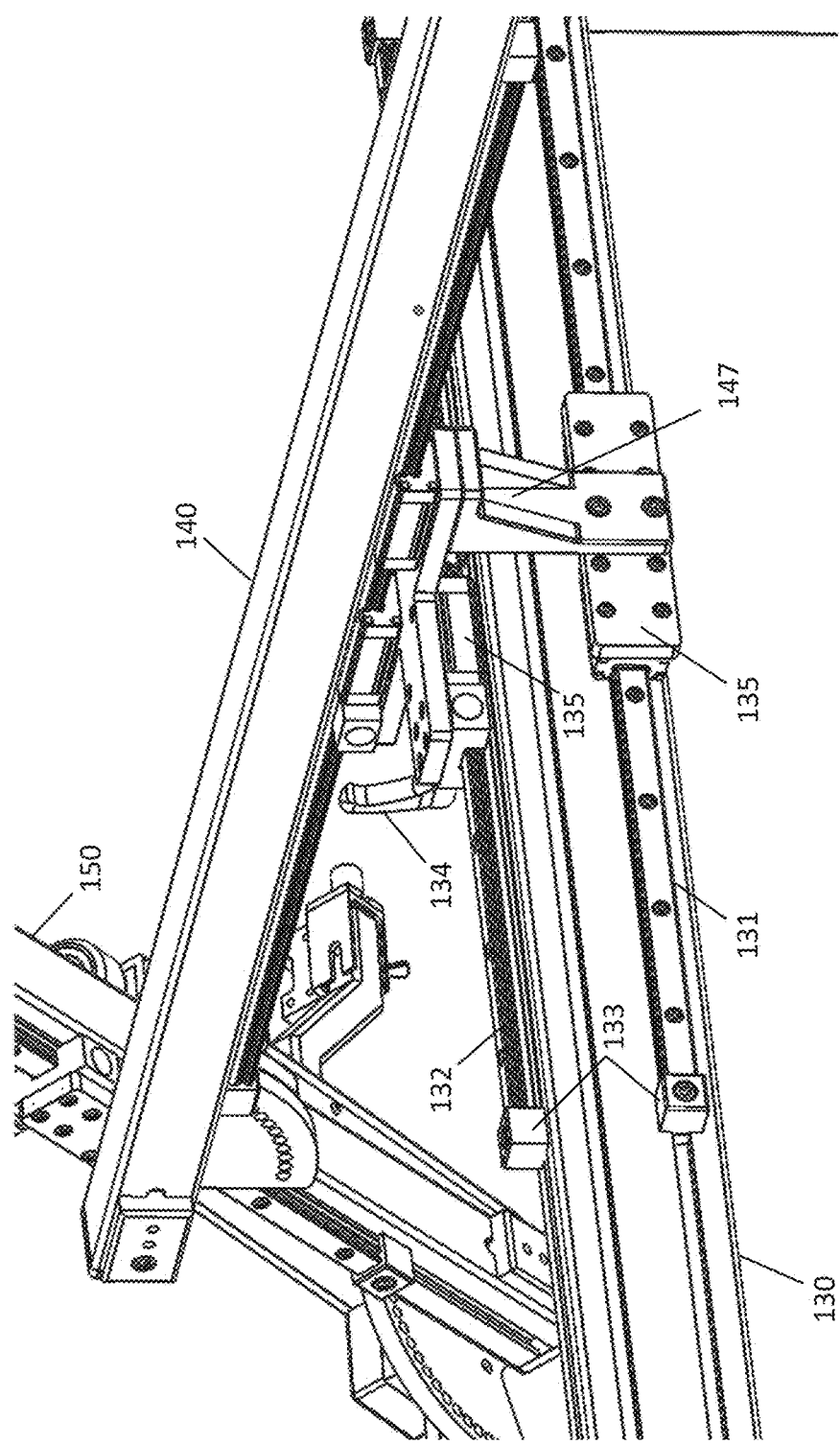
FIG. 8 depicts a view of an illustrative connection of a cross beam and arm connection according to an embodiment.

Referring now to FIG. 8, an illustrative connection between a station cross beam 130 and at least one station arm 140 and 150 is shown. In one embodiment, the connection may include a lower rail 131, an upper rail 132, one or more rail stoppers 133, a cross beam x-axis lock feature 134, and a rider(s) 135. In one embodiment, the station cross beam 130 may be the main beam of the station 100 and run parallel to the x-axis (FIG. 1). Thus, the station cross beam 130 allows full control over the location of the distal end 101 of the station 100 in the x-axis.

In a further embodiment, movement of the long station arm 140 along the station cross beam 130 in the x-axis may be performed using a rail system (e.g., one rail, two rails, three rails, etc.) 131 and 132 that is attached to the station cross beam. In one embodiment, the station arms 140 and 150 are attached to rider(s) 135, and the rider(s) move on the station cross beam 130. In a further embodiment, the movement of the rider(s) 135 may be restricted via a cross beam x-axis lock feature 134, which may lock the arms in a fixed position. Thus, an embodiment may require the opening of the cross beam x-axis lock feature 134 in order for any movement in the x-axis to take place.

In another embodiment, multiple riders (e.g., one, two, three, etc.) 135 may be attached to a single rail within the rail system (e.g., in parallel or series). The use of multiple riders 135 attached to one another is designed to provide increased stability and minimal movement when a load is applied to the distal end 101 of the station 100. In a further embodiment, the station cross beam 130 width may be smaller (e.g., 500 mm, 600 mm, 700 mm, etc.) for narrow operating room beds, and larger (e.g., 1300 mm, 1400 mm, 1500 mm, etc.) for wide operating room beds.

Figure 9:
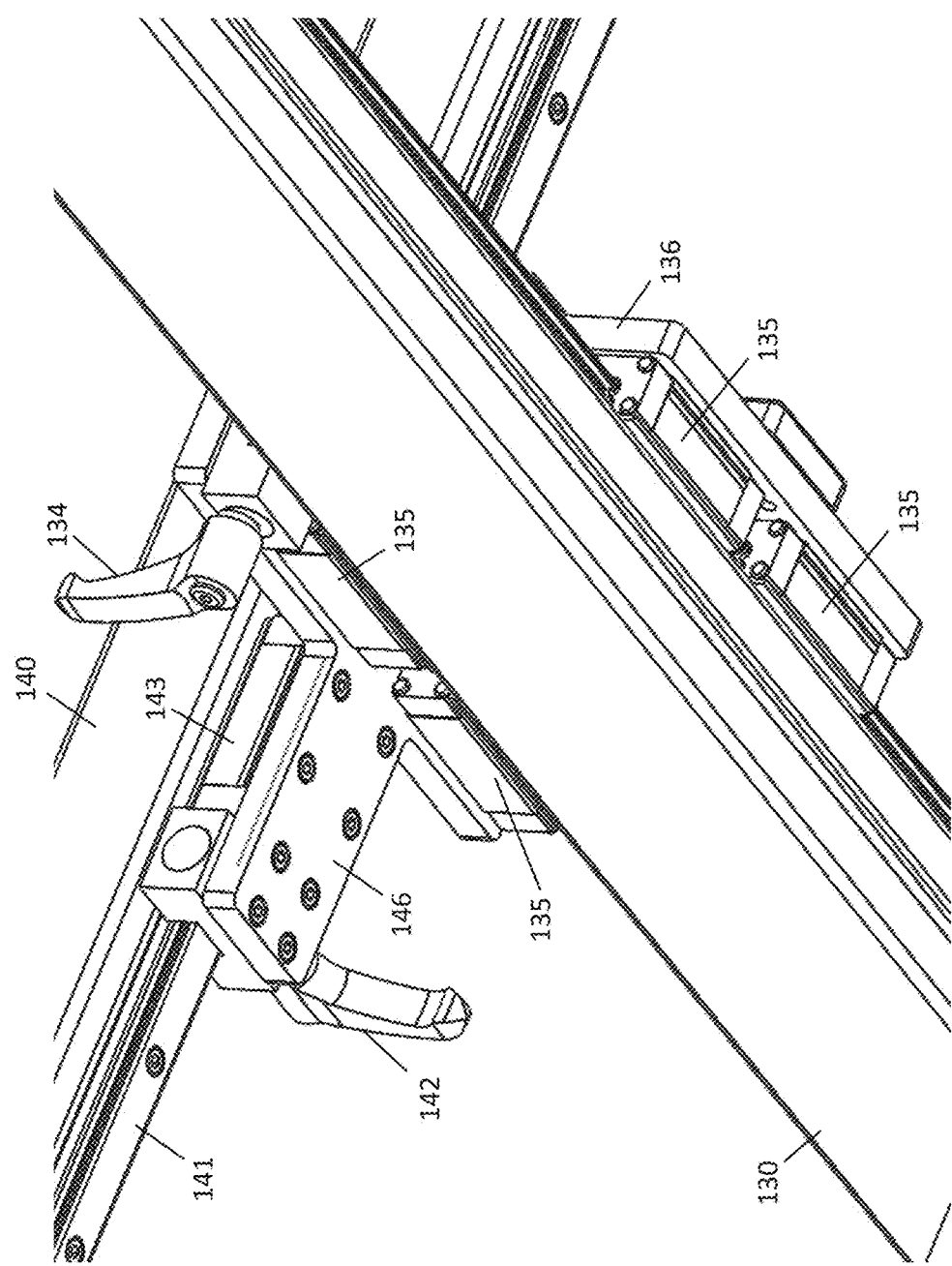
FIG. 9 depicts another view of an illustrative connection of a cross beam and arm connection according to an embodiment.
Figure 10:
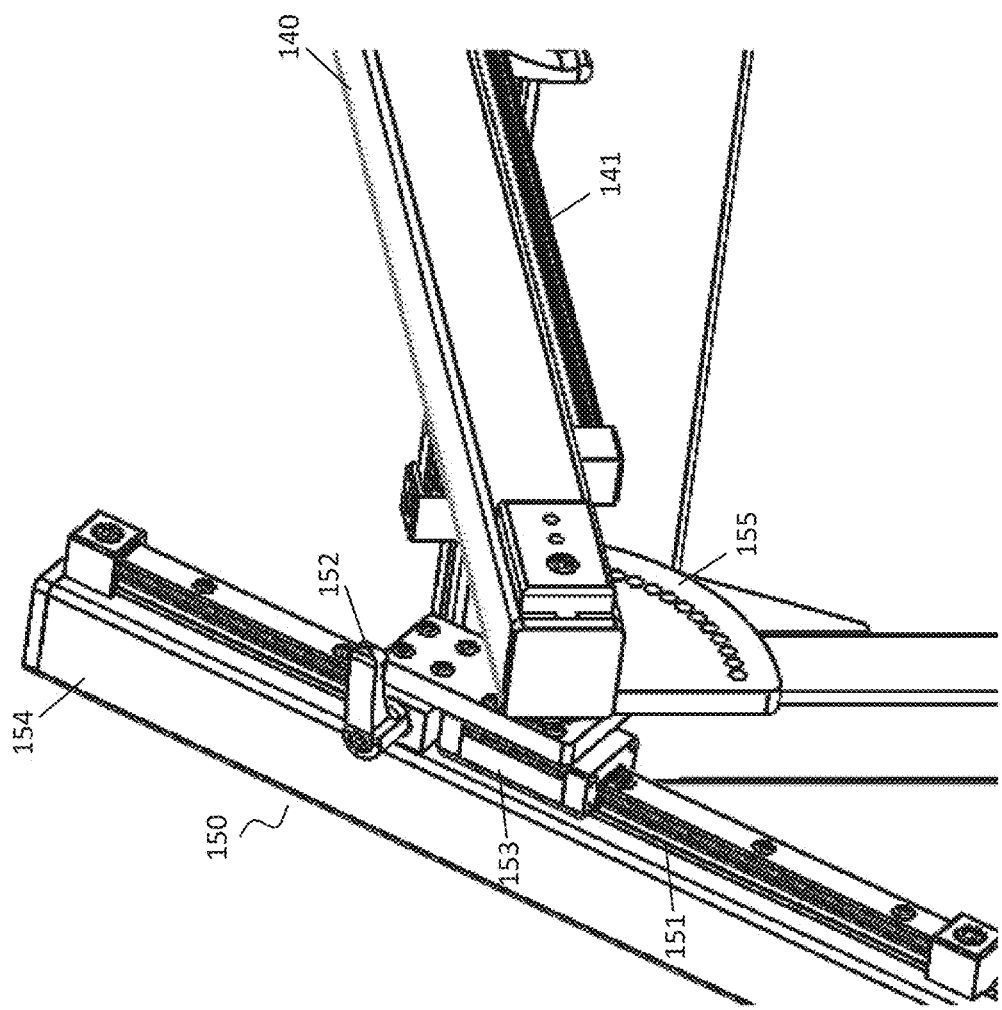
FIG. 10 depicts a view of an illustrative connection of a short arm and a long arm according to an embodiment.
Figure 11:
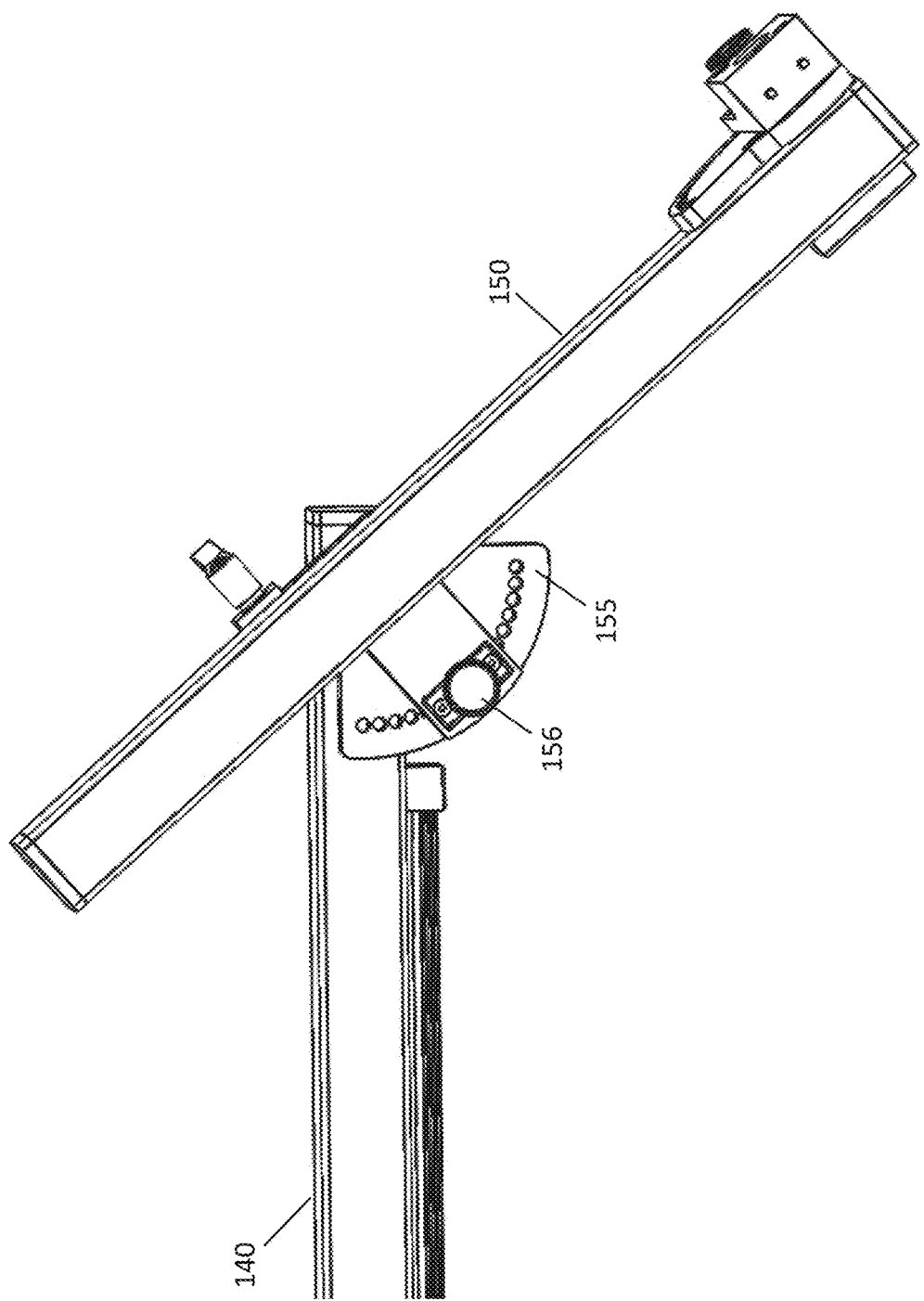
FIG. 11 depicts another view of an illustrative connection of a short arm and a long arm according to an embodiment.
Figure 12:
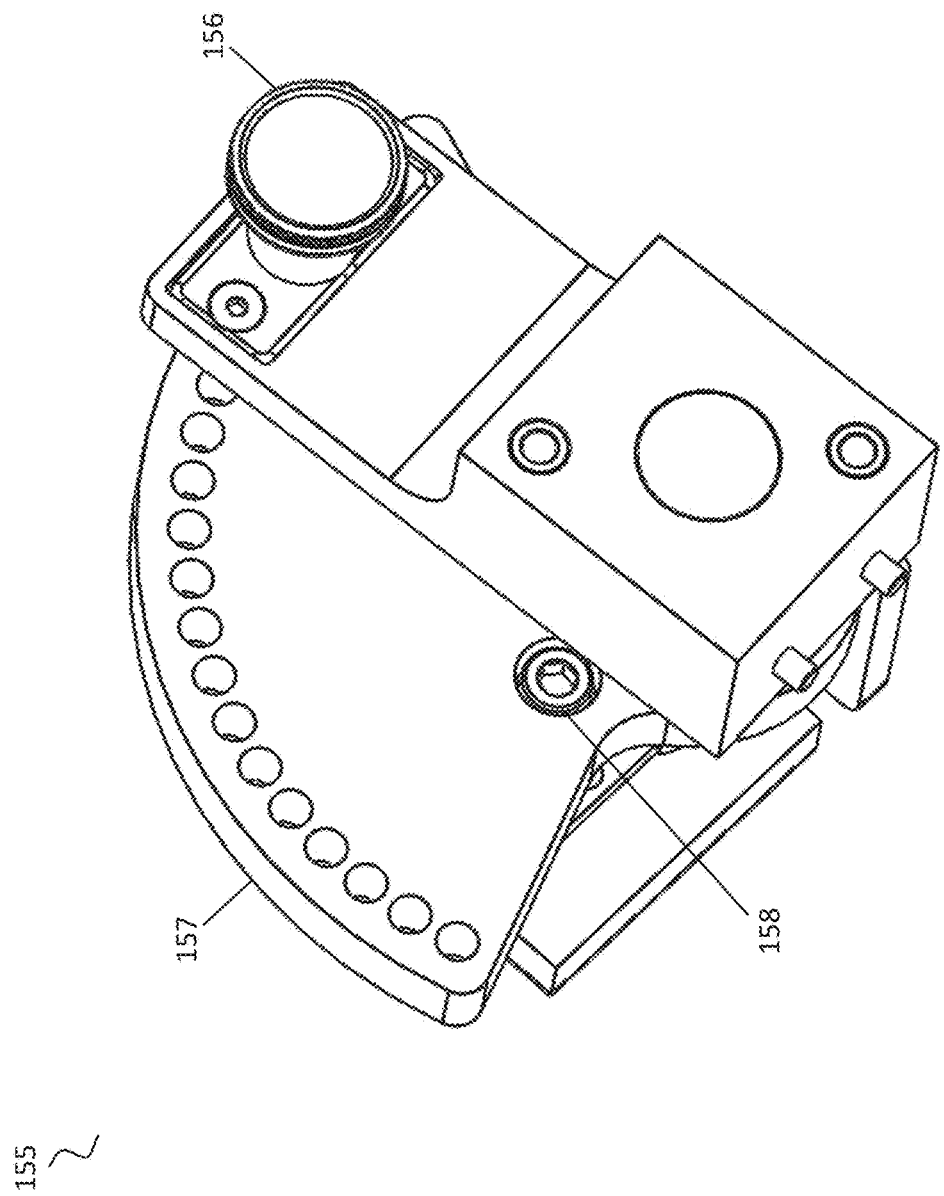
FIG. 12 depicts a view of an illustrative discrete rotation joint according to an embodiment.

Referring now to FIG. 9, an illustrative station arm (e.g., the long station arm 140) and station cross beam 130 beam connection is shown. In one embodiment, the station arm (e.g., the long station arm 140) may include a long arm y-axis rail 141, a cross beam y-axis movement lock 142, a y-axis rider 143, and a plate (e.g., a metal, stainless steel, aluminum, etc.) 146. In another embodiment, the station cross beam 130 may include a cross beam x-axis lock feature 134, one or more x-axis rider(s) 135, and a plate (e.g., a metal, stainless steel, aluminum, etc.) 136. The station cross beam 130 attachment to the long station arm 140 may be done via various parts (e.g., plates 136 and 146, rider(s) 135 and 143, and locking features 142 and 134).

Thus, in one embodiment, the rider(s) 135 and 143 may connect via a plate 136 and 146, which, in turn, is connected on one side to the long station arm 140. The plates 136 and 146 may also contact the cross beam upper rail 132 on the other side. In addition, a plate 136 may be connected to a rider(s) 135 that is attached to the lower rail 131. In one embodiment, the two plates 136 and 146 may be attached via a third metal plate (147 see FIG. 8). The third metal plate 147 provides not only a connection to the first two plates (e.g., metal plates) but also stability. The third metal plate 147 also helps to minimize any movement of the long station arms 140 when the locks features 134 and 142 are in the closed configuration.

Another embodiment, as shown in FIGS. 10-13, allows rotational joint movement between two arms (e.g., the short arm and the long arm). An embodiment that utilizes a rotational joint may include a long station arm 140, a short station arm 150, a short arm rail 151, a short arm locking feature 152, a short arm rider 153, a short arm rack 154, a discrete rotation joint 155, and a plunger/locking pin 156. In a further embodiment, the discrete rotation joint 155 may be affixed to the long station arm 140 via one or more screws 158 placed in one or more recessed cavities 159.

Figure 13:
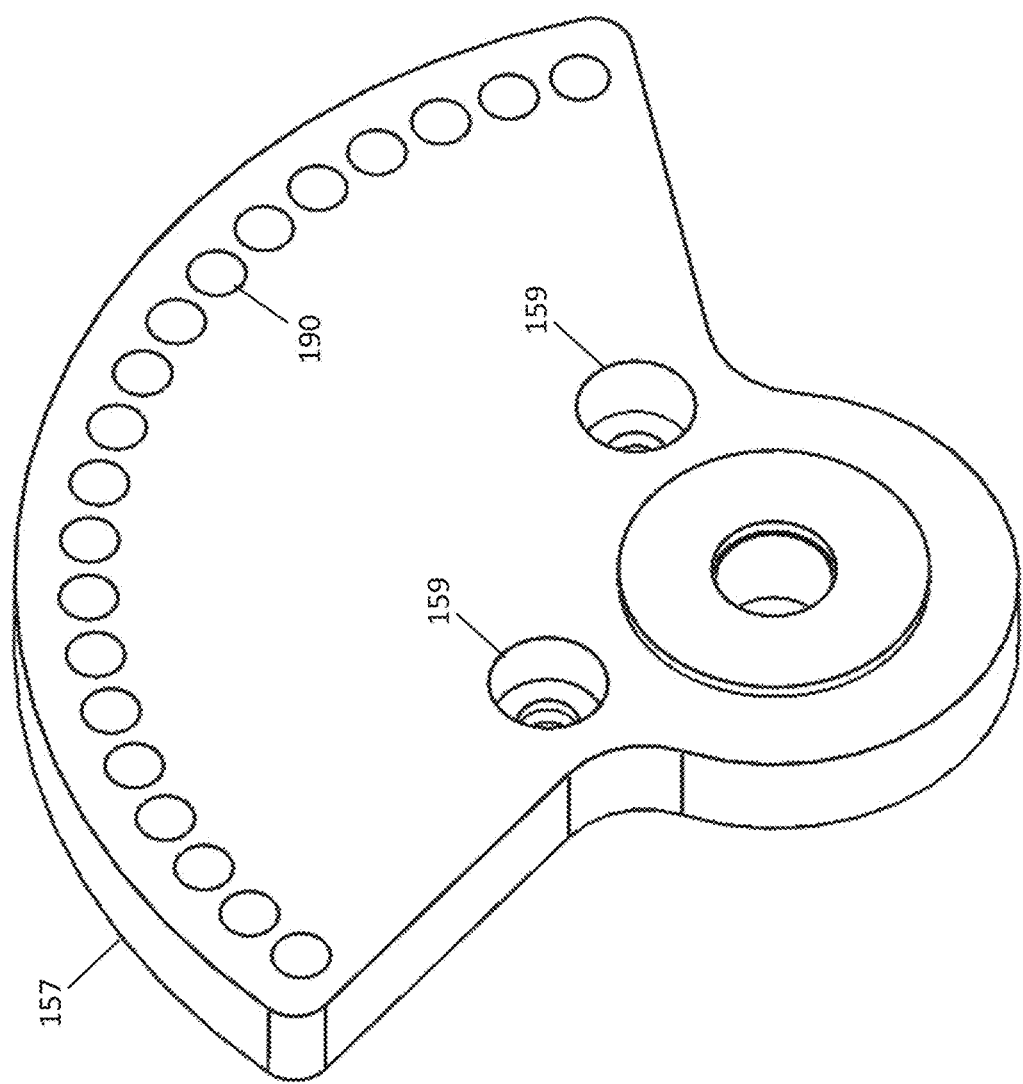
FIG. 13 depicts a view of another illustrative discrete rotation joint according to an embodiment.

In one embodiment, the discrete rotation joint 155 is normally locked in a fixed position by a pivot pin on a plunger/locking pin 156. When an operator wishes to rotate the short station arm 150, the operator may operate the plunger/locking pin 156 (e.g., pull the plunger pin out of the locking hole(s) 190 it is currently in) to rotate the short station arm 150 and re-lock it into one of the locking hole(s). The locking plate 157 can be attached to the short station arm 150 in different orientations that are set according to the one or more recessed cavities 159 selected. It should be understood, that the figures are for illustrative purposes only, and thus although only two cavities are shown in FIG. 13, an embodiment may have more or fewer depending on the desired flexibility. In one embodiment, the combination of locking plate 157 orientation and selection of locking hole(s) 190 can allow for 270 degrees of movement in the short station arm 150.

In another embodiment, the short station arm 150 may be moved along the short arm rail 151 by opening the short arm locking feature 152, moving the rail using the short arm rider 153, and closing the short arm locking feature 152. Additionally or alternatively, an embodiment may move the short station arm 150 using various other techniques (e.g., electrical motors, pneumatic motors, electrical pistons, pneumatic pistons, electromagnets, etc.) or combinations of various techniques. In addition, a discrete locking feature may be added to ensure that the arm is in a locked position as long as the discrete locking feature is not pulled out of location.

Figure 14:
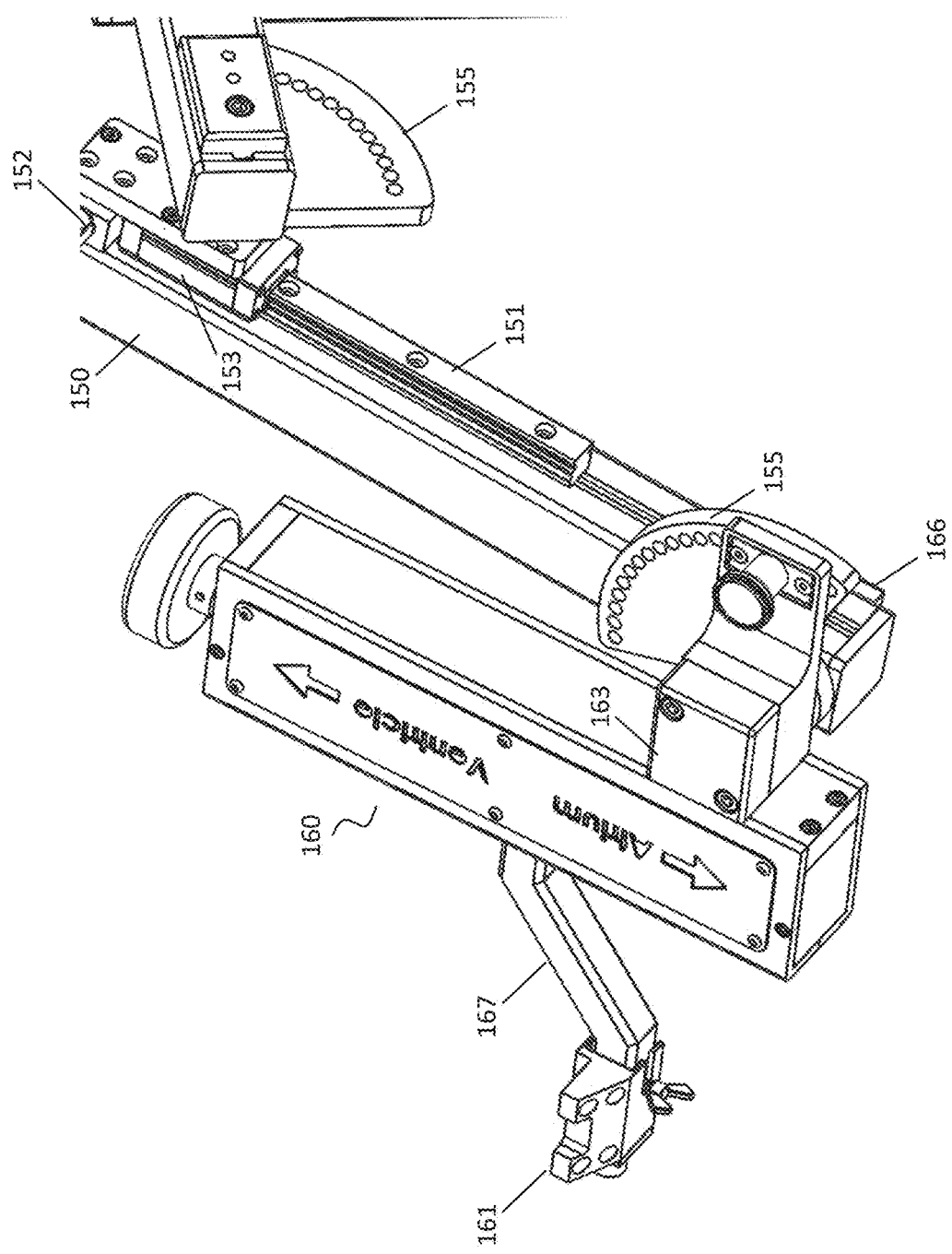
FIG. 14 depicts a view of an illustrative connection of an axial member with a short arm according to an embodiment.

Referring now to FIG. 14, an illustrative axial connection with the short station arm 150 is shown. In one embodiment, the connection may include a short station arm 150, a short arm rail 151, a short arm locking feature 152, a short arm rider 153, a discrete rotation joint 155, an axial member 160, an axial connector 161, an axial to short arm connecting area 163, a support arm attachment plate 166, and an axial connecting bar 167. As discussed herein, an embodiment may allow for movement of the axial member 160 using the discrete rotation joint 155 (e.g., rotational movement) and the short arm rider 153 as well as various other devices not pictured in FIG. 14, but discussed herein.

Figure 15:
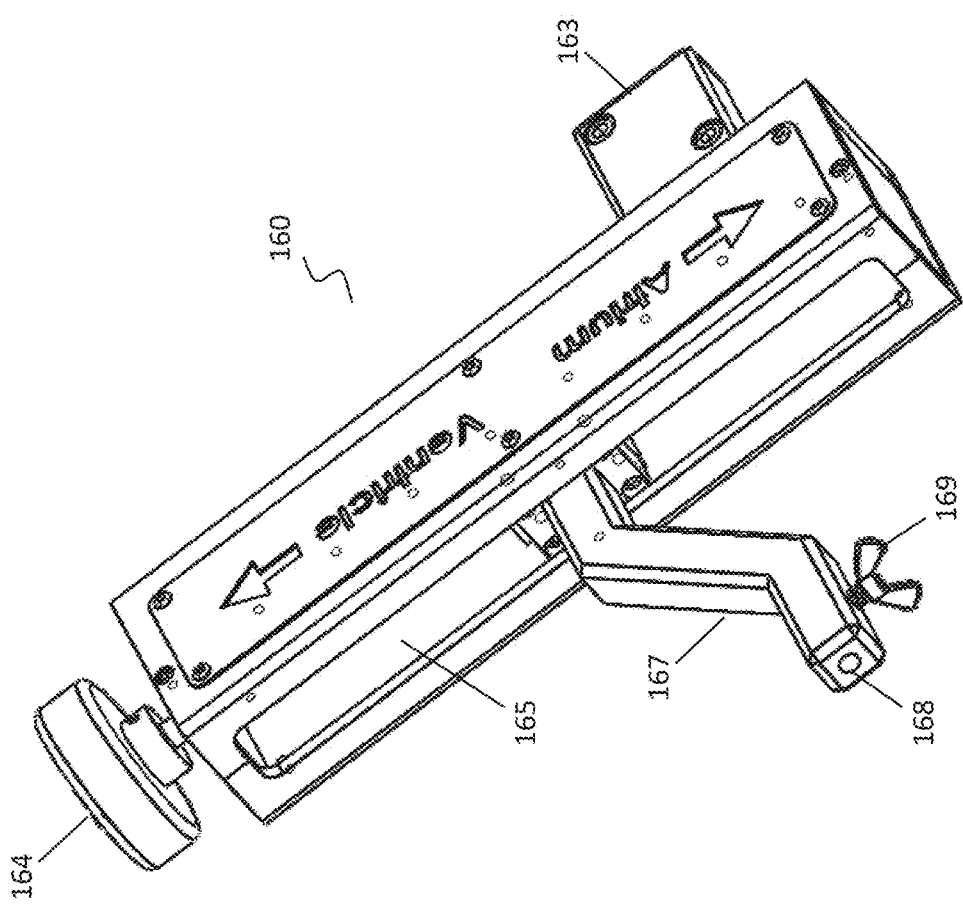
FIG. 15 depicts a view of an illustrative axial member according to an embodiment.

Now referring to FIG. 15, an illustrative example of an axial member 160 is shown. In one embodiment, an axial member 100 may include an axial to short arm connecting area 163, an axial main knob 164, an axial rail 165, an axial connecting bar 167, an axial connecting bar distal end 168, and an axial bar locking screw 169. As discussed herein, the axial member has a large range of movement that allows the distal end 101 of the station 100 to be positioned with the best possible access to the target site as well as inside the target (e.g., the heart chamber).

Figure 17:
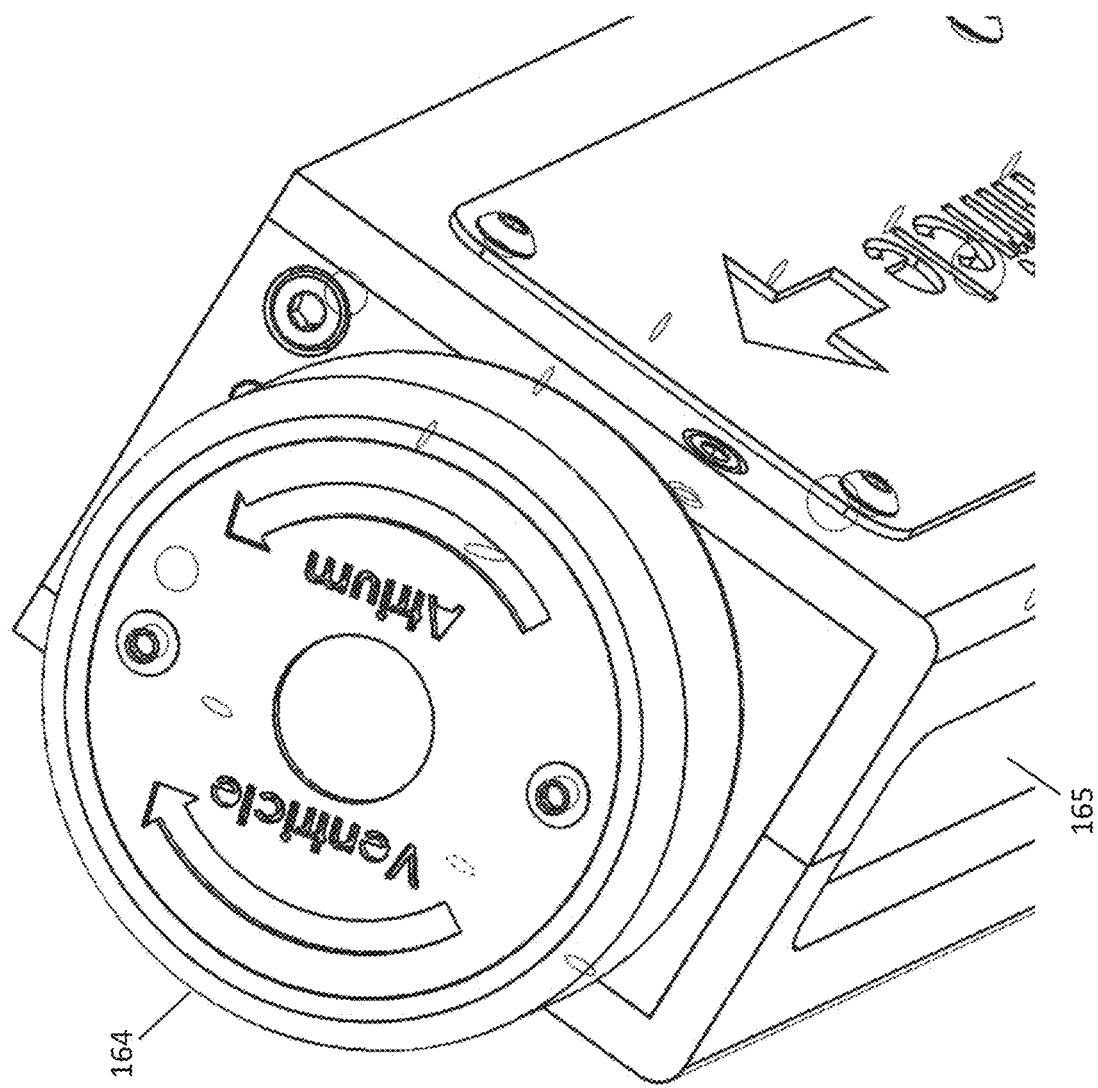
FIG. 17 depicts detail view of an illustrative axial main knob according to an embodiment.

In one embodiment, the movement may be performed by rotating the axial main knob 164 (e.g., clockwise), which may cause the connecting bar 167 to move in a direction along the axial rail 165. The connecting bar 167 may move in both directions along the axial rail 165 based on the direction in which the axial main knob 164 is rotated (e.g., clockwise rotation mat move the bar up, and counter-clockwise rotation may move the bar down). A more detailed view of an illustrative axial main knob 164 in conjunction with the axial member 160 is shown in FIG. 17.

Figure 16:
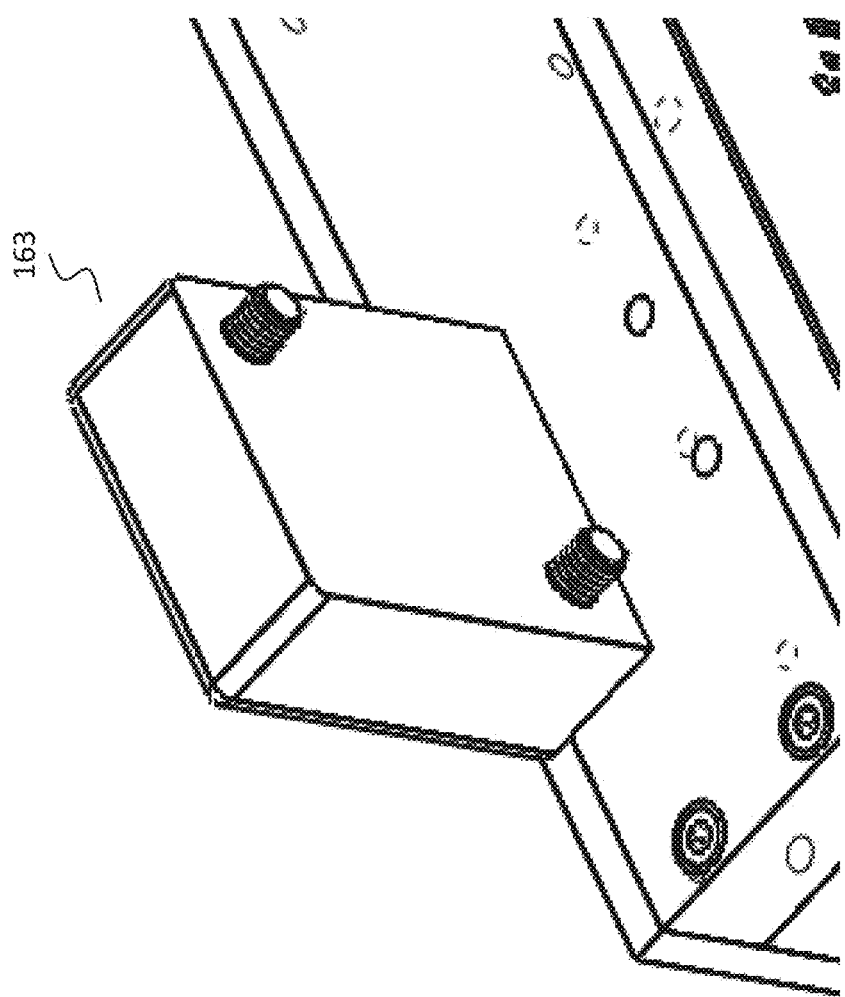
FIG. 16 depicts a detail view of an illustrative axial connecting area according to an embodiment.

The attachment of the axial member 160 to the short station arm 150 may be formed using a connecting feature (e.g., the axial to short arm connecting area 163). In one embodiment, the connecting feature may be a plate attached with screws to the short station arm 150, such as is shown in FIG. 15. Additionally or alternatively, the attachment may be made directly or through drapes in order to increase sterility. A more detailed view of an illustrative connecting feature, specifically an axial to short station arm 150 connecting area 163, is shown in FIG. 16.

In another embodiment, the stroke of the axial member 160 may be in the range of about 40 mm to about 600 mm. Thus, it may be used in combination with the movement of the short station arm 150 and the axial member 160 by aligning them and moving them in the same direction. The axial movement can be performed manually or using various techniques (e.g., electrical motors, pneumatic motors, electrical pistons, pneumatic pistons, electromagnets, etc.) or combinations of various techniques.

Figure 18:
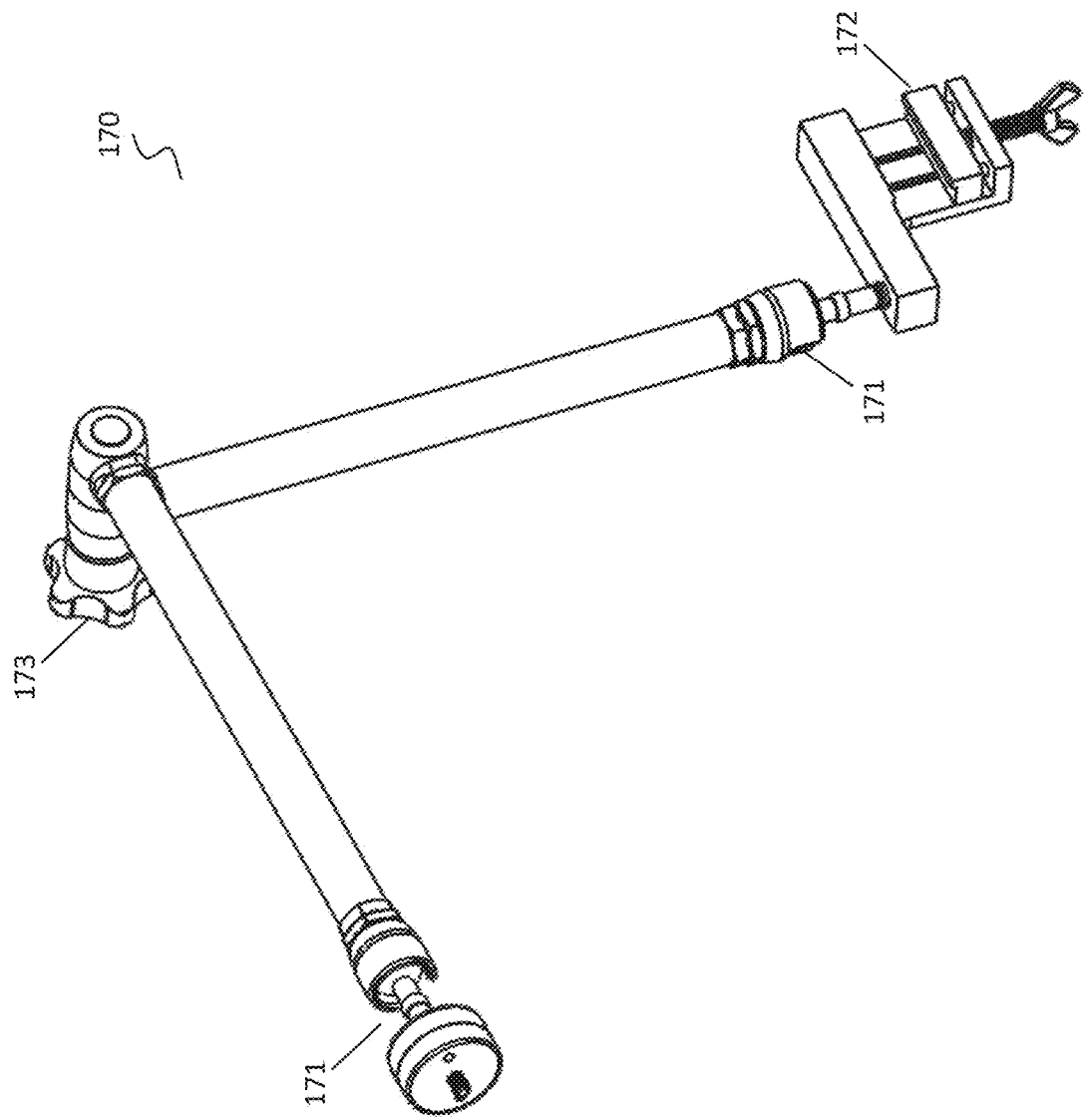
FIG. 18 depicts a perspective view of an illustrative support arm according to an embodiment.
Figure 19:
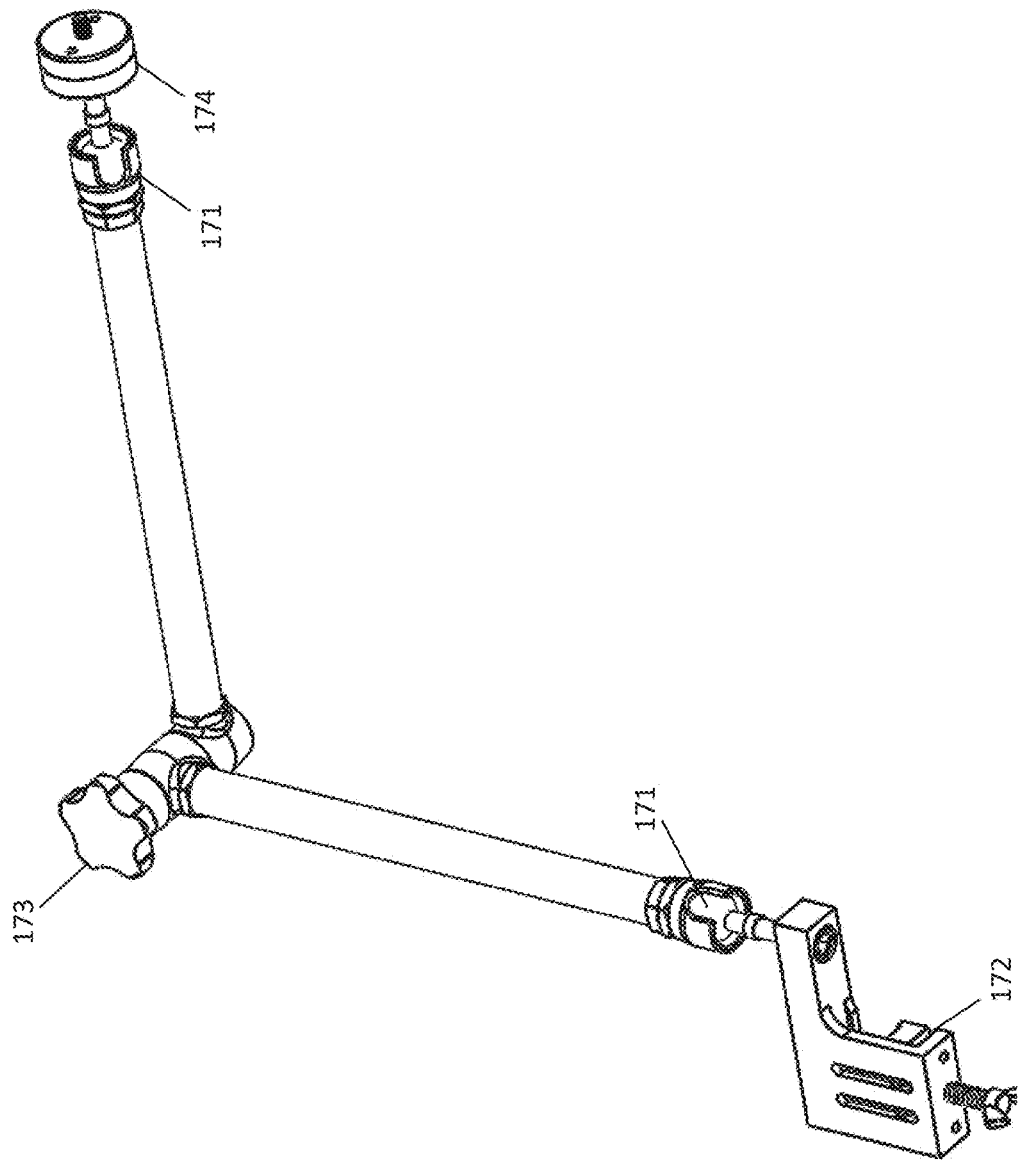
FIG. 19 depicts another perspective view of an illustrative support arm according to an embodiment.
Figure 20:
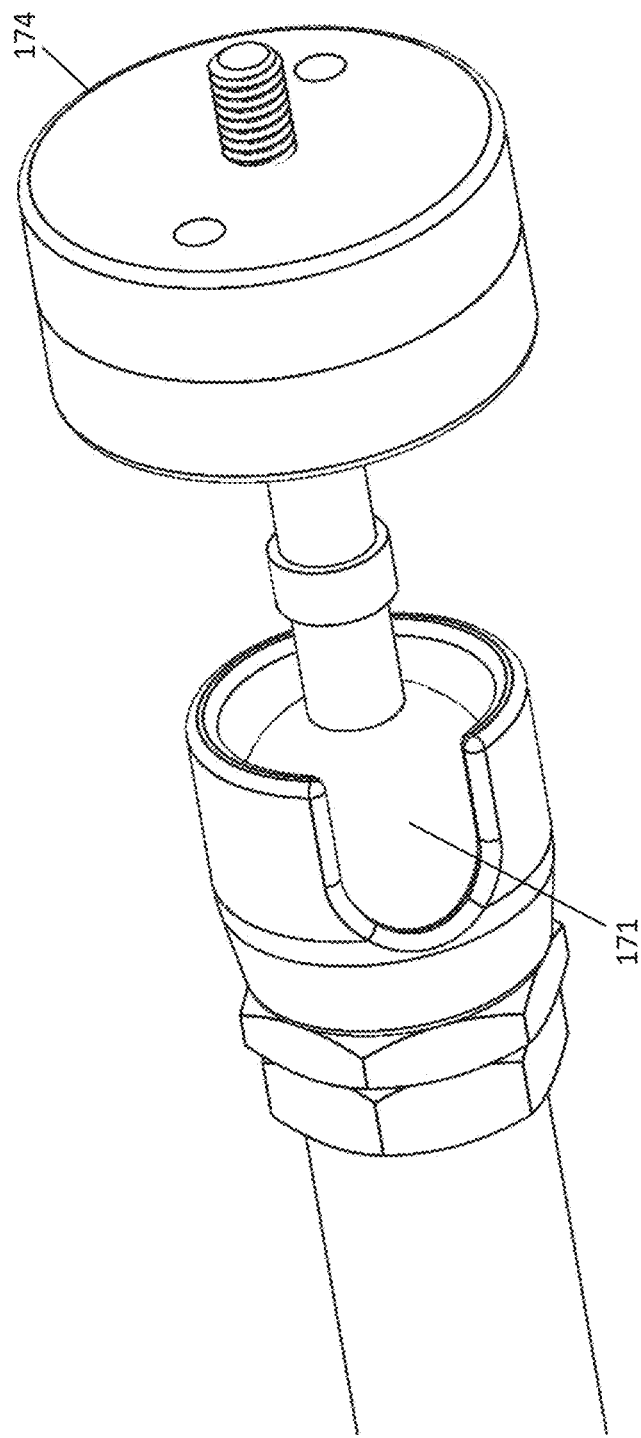
FIG. 20 depicts a detail view of an illustrative ball joint and axial plate connector according to an embodiment.
Figure 21:
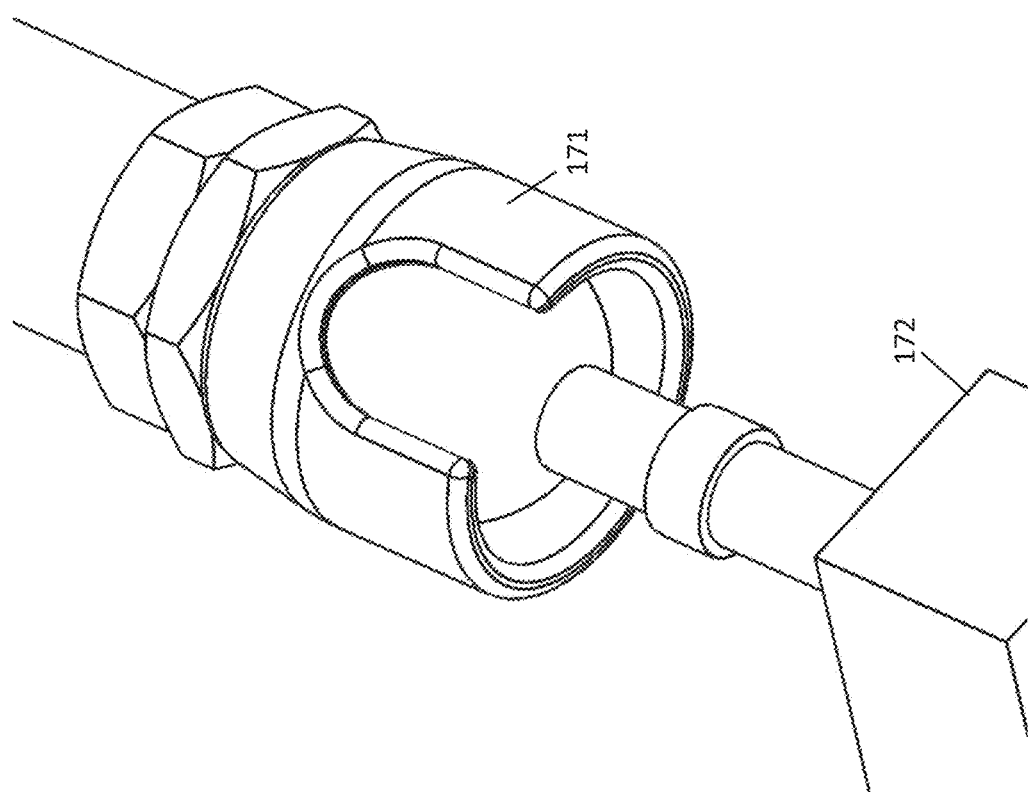
FIG. 21 depicts a detail view of an illustrative ball joint and an operating room bed attachment according to an embodiment.

Now referring to FIG. 18, an illustrative example of a support arm 170 is shown. In one embodiment, a support arm 170 may include a ball joint 171, an operating room bed attachment 172, a support arm lock knob 173, and an axial plate connection 174. FIGS. 18-24 illustrate embodiments of a support arm 170. In one embodiment, the support arm 170 may provide additional support to the station 100. It is critical that equipment used during invasive procedures have minimal to no movement in order to ensure the safety of the patient. Thus, an embodiment may utilize the support arm 170 to ensure that minimal movement is imparted to the delivery system during the performance of any clinical procedure (e.g., a structural heart procedure). In a further embodiment, the station 100 may have more than one support arm 170 to increase stability of the distal end 101.

Figure 22:
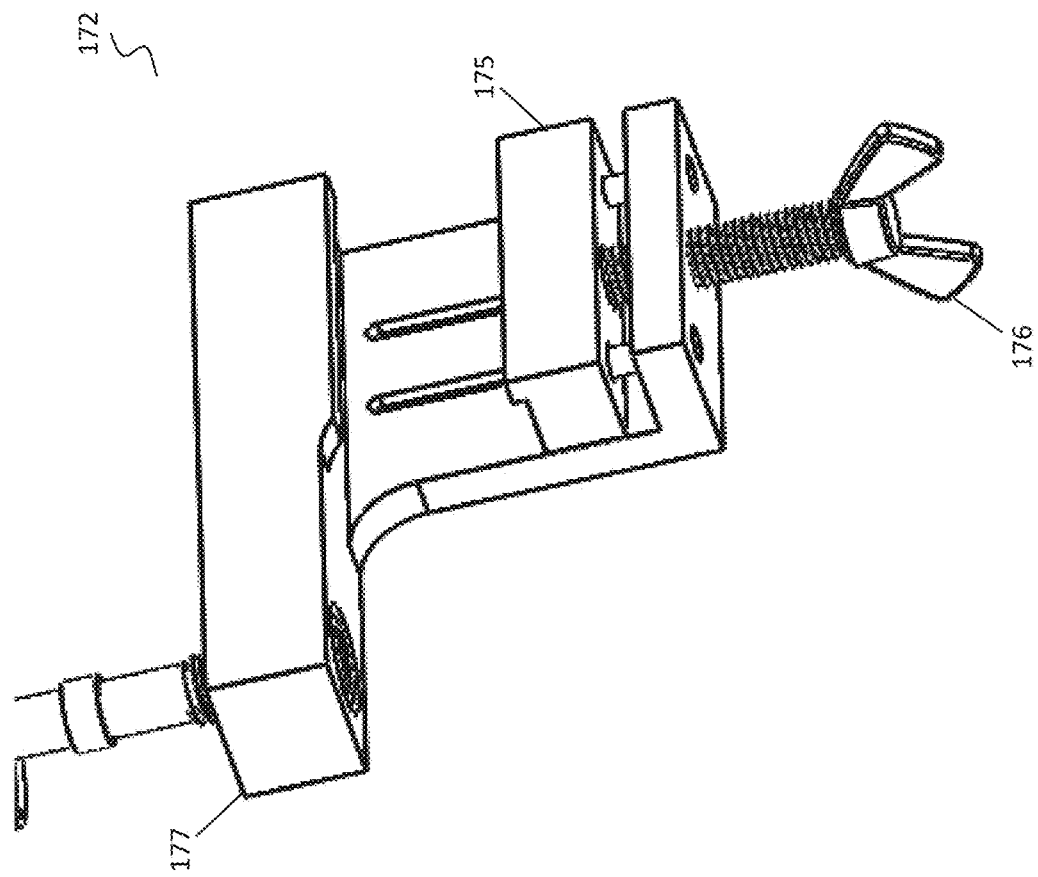
FIG. 22 depicts a detail view of an illustrative operating room bed attachment according to an embodiment.
Figure 29:
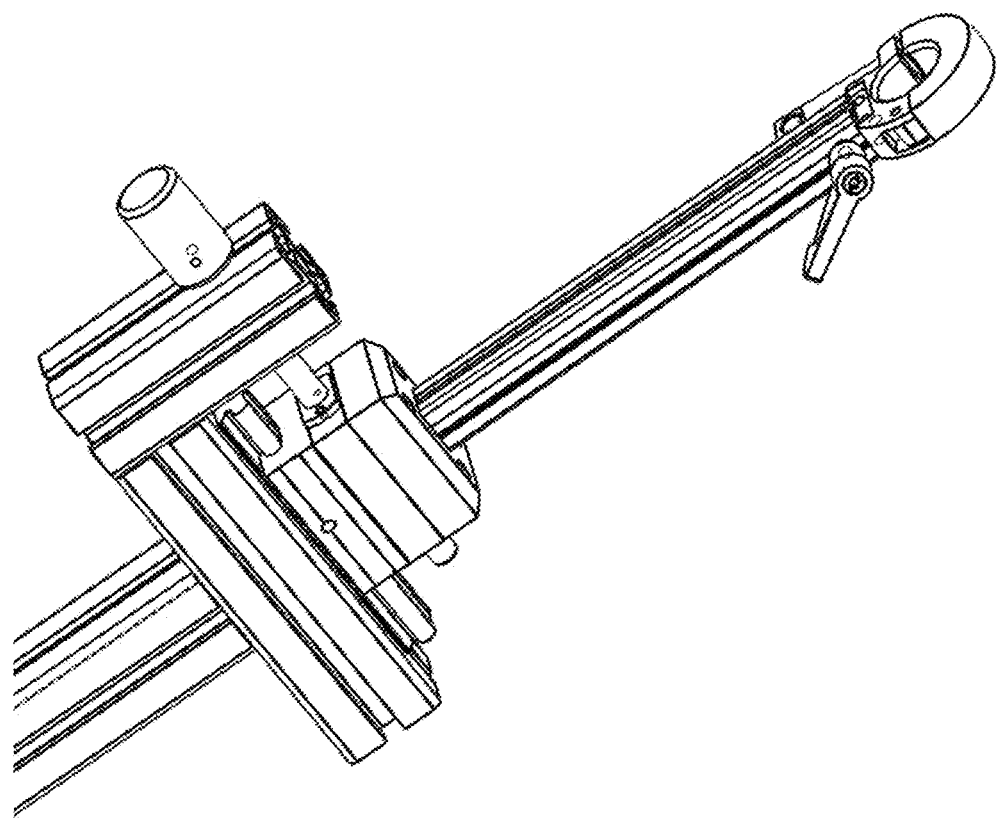
FIG. 29 depicts a view of an illustrative axial member and ball joint according to an embodiment.
Figure 30:
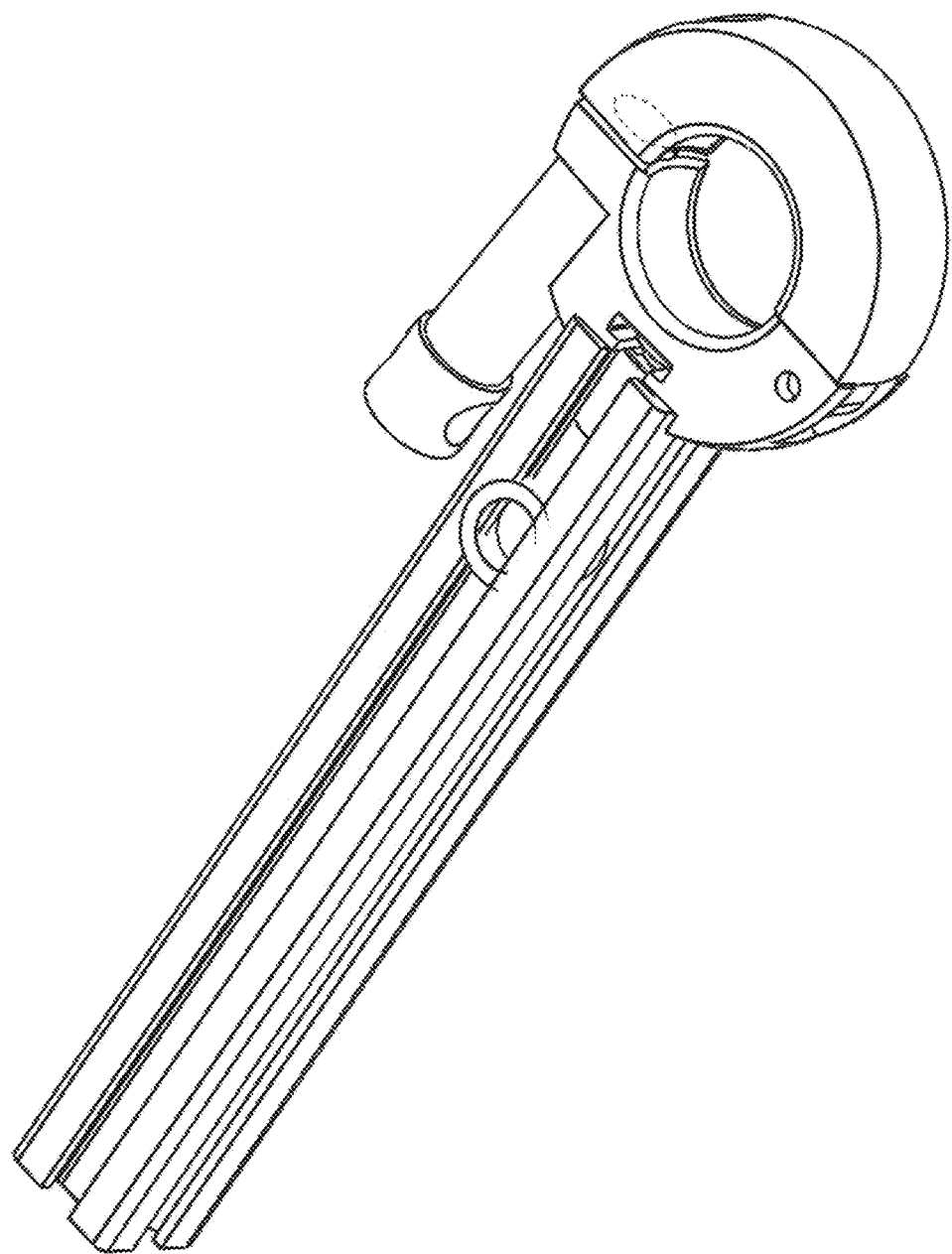
FIG. 30 depicts a view of an illustrative ball joint according to an embodiment.
Figure 31:
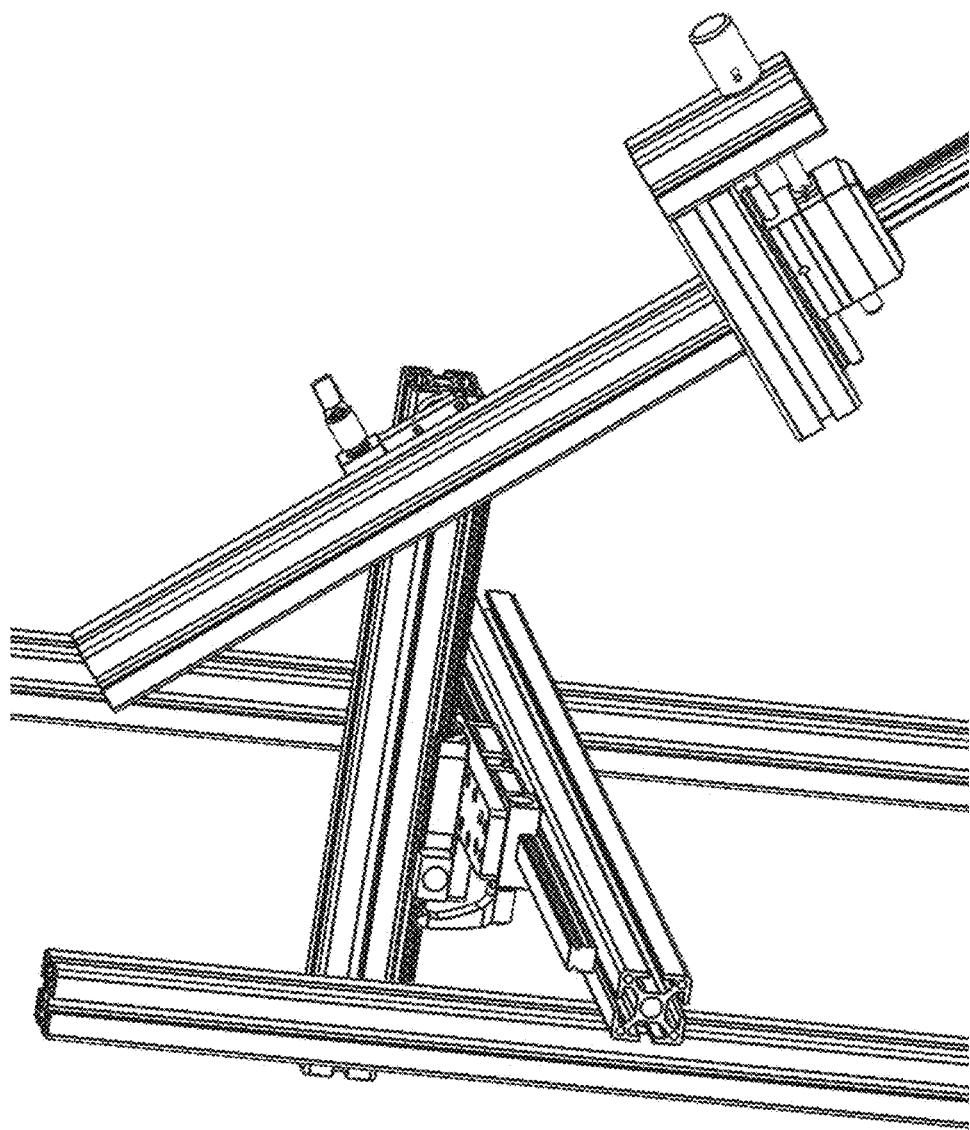
FIG. 31 depicts a view of an illustrative friction rotation joint according to an embodiment.
Figure 32:
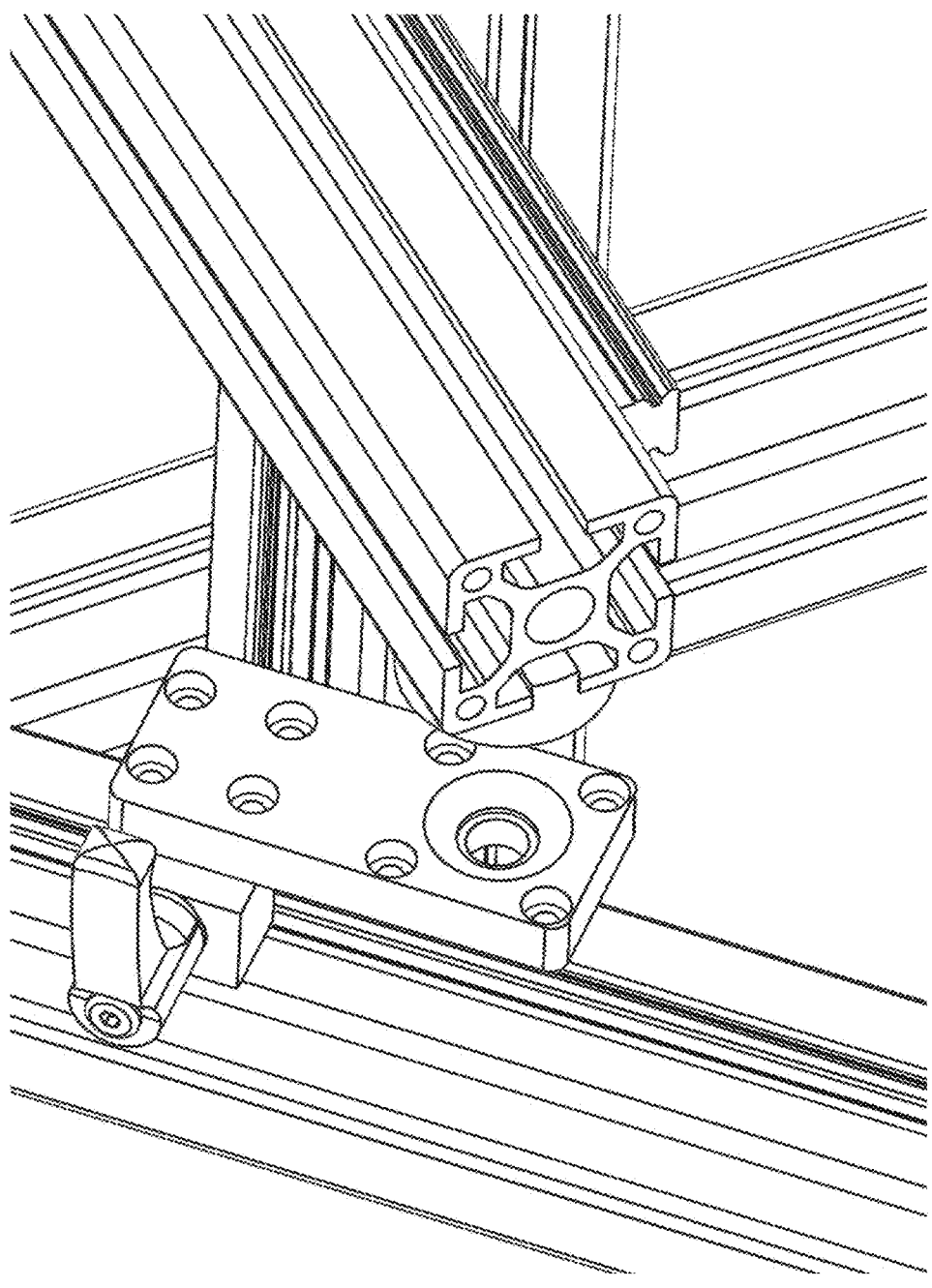
FIG. 32 depicts a view of an illustrative rotation joint plate according to an embodiment.
Figure 33:
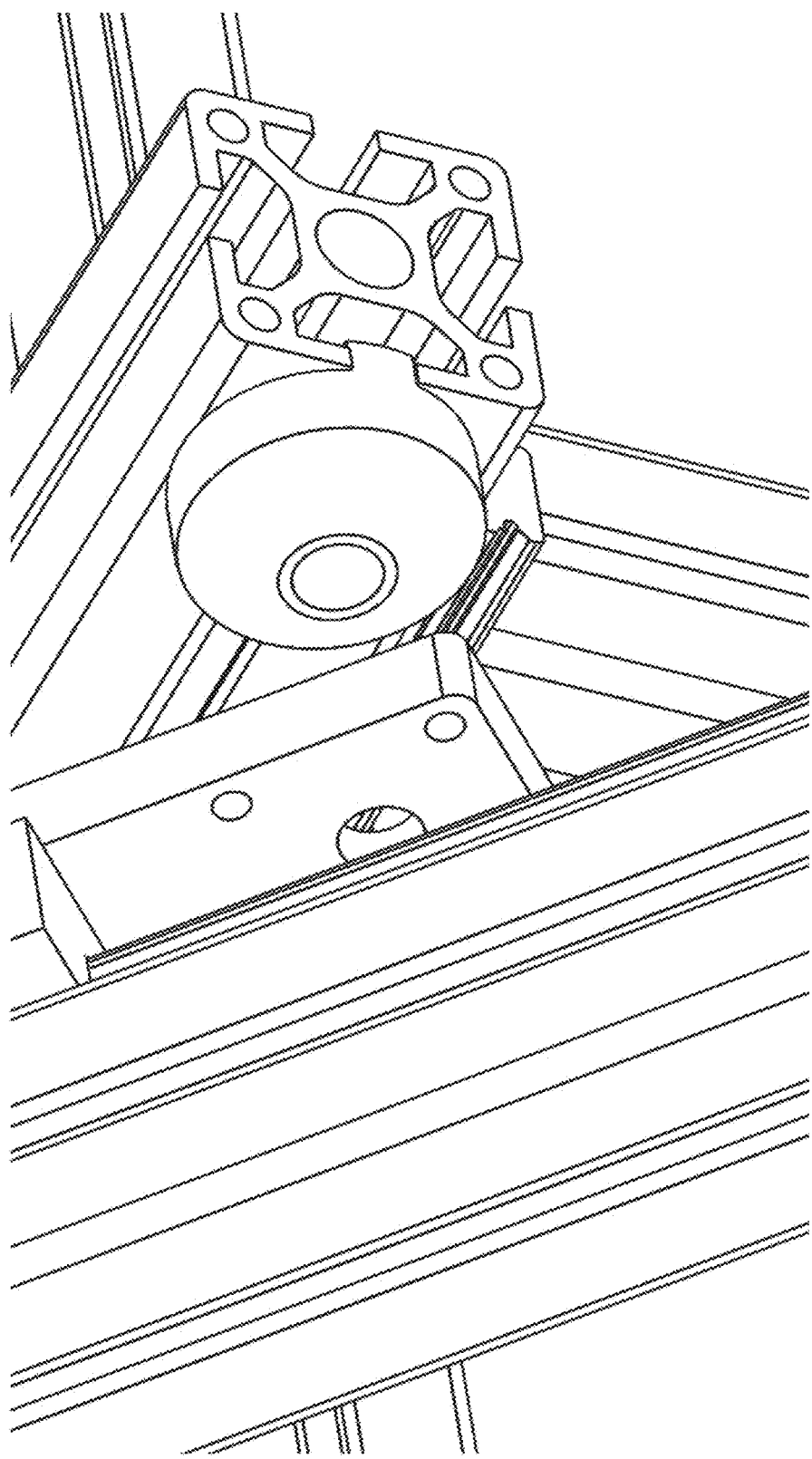
FIG. 33 depicts a view of an illustrative rotational joint cone according to an embodiment.

Turning now to FIG. 22, an illustrative operating room bed attachment 172 is shown. In one embodiment, attachment of the support arm 170 to the operating room bed may be performed using the operating room bed attachment 172 that fits (e.g., is specifically designed for) a particular operating room bed rail 111. As discussed herein, the operating room bed rail 111 may have a width in the range of about 5 mm to about 15 mm and a height in the range of about 12 mm to about 30 mm (as shown in FIG. 3). Locking the operating room bed attachment 172 to the operating room bed rail 111 may be performed by tightening a support arm connecting block 175 using a threaded screw system 176. However, it should be understood that the illustration in FIG. 22 is only one possible embodiment and that various other embodiments may be used (e.g., using a clamp (see FIG. 29) or other method that will lock it into a fixed position).

Brief reference will now be made to FIGS. 23 and 24. In order to ensure proper stability of the axial member 160, an embodiment may attach the support arm 170 to the axial using the axial plate connection 174. The axial plate connection 174 may be directly connected to the support arm attachment plate 166, as shown in FIGS. 23 and 24. In one embodiment, the connection may be direct, as discussed, as long as both parts are sterile. Additionally or alternatively, the connection 174 between the axial plate and the support arm attachment plate 166 may be through a drape if either of the components is not sterile.

Figure 25:
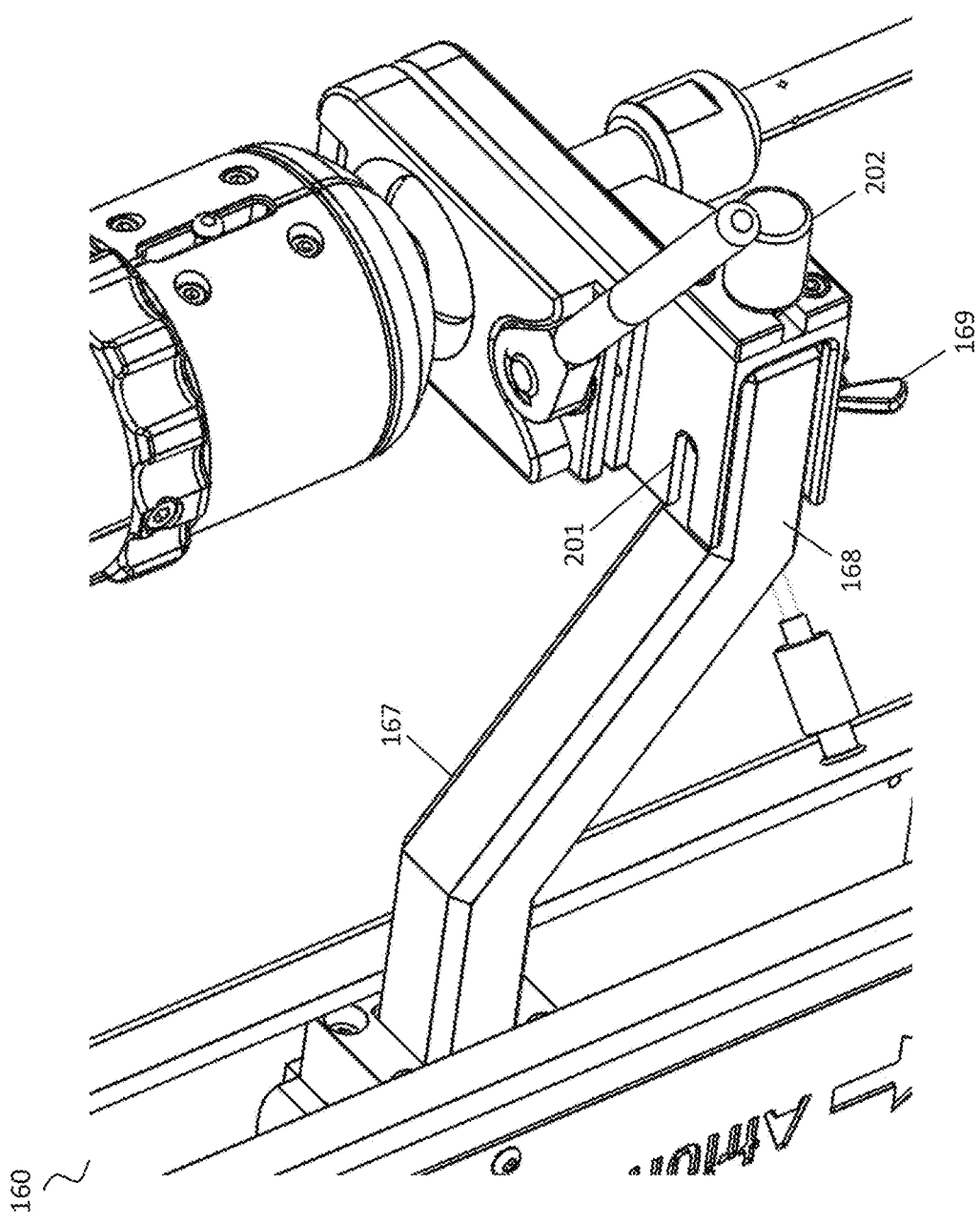
FIG. 25 depicts a view of an illustrative connection of a delivery system and an axial member according to an embodiment.
Figure 26:
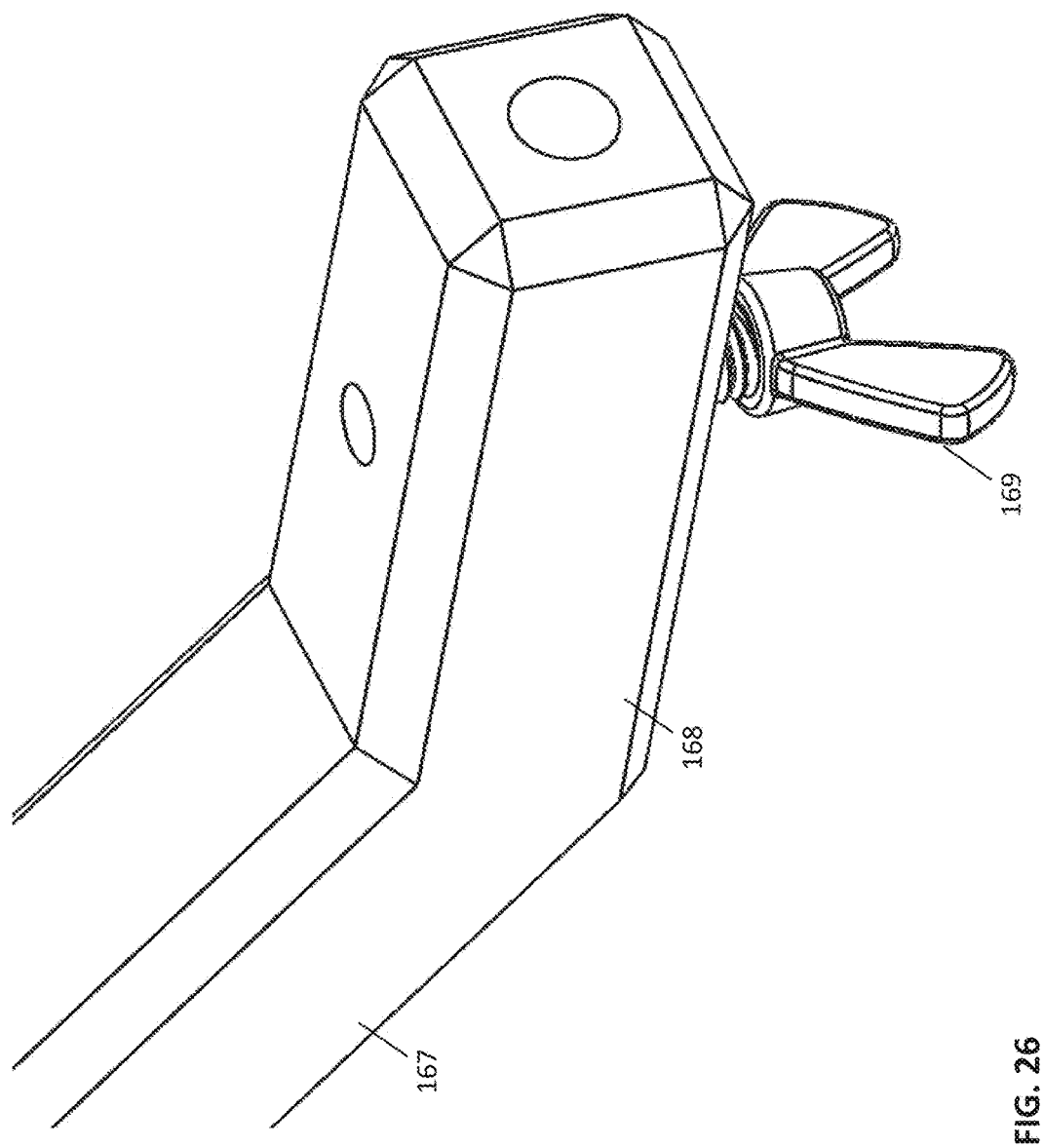
FIG. 26 depicts a view of an illustrative distal end of an axial member connecting bar according to an embodiment.
Figure 27:
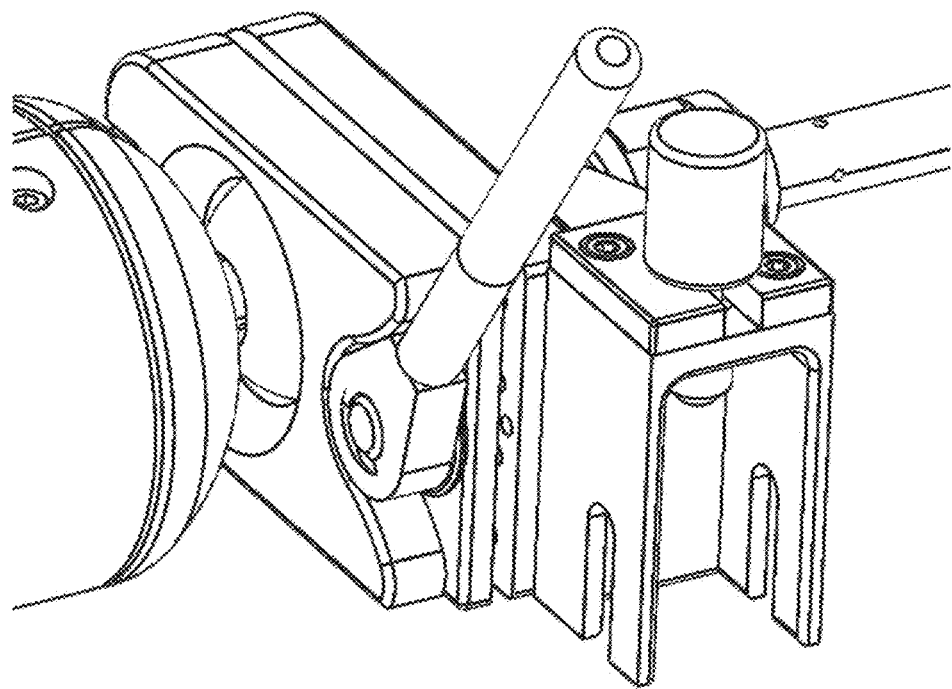
FIG. 27 depicts a view of an illustrative interface with a delivery system according to an embodiment.
Figure 28:
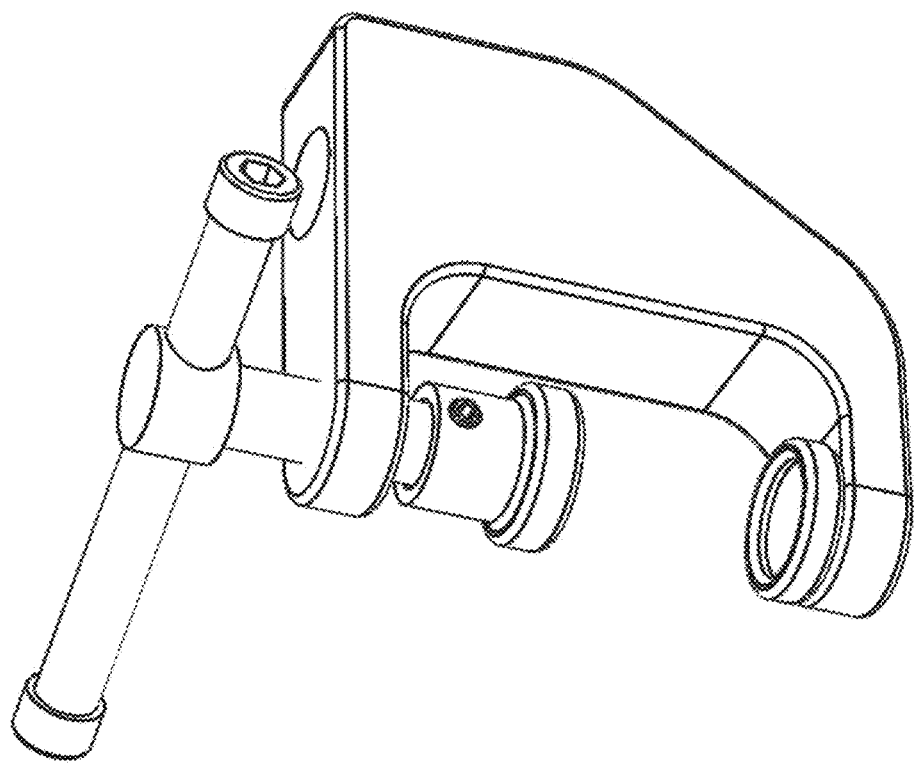
FIG. 28 depicts a view of an illustrative clamp mechanism according to an embodiment.

In FIG. 25, an illustrative connection between a delivery system (DS) and an axial member 160 is shown. In one embodiment, the connection may include an axial connector knob 202, an axial connecting bar 167, an axial distal end bar connector 201, and an axial bar locking screw 169. FIGS. 25-27 show further details and embodiments of the delivery system and axial member connection. The connection may be formed by attaching a ball joint that is part of the delivery system attached to the axial connector 161 to the axial connecting bar distal end 168 during a procedure. In one embodiment, this attachment is performed by closing the axial connector knob 202 and locking the axial bar locking screw 169. Additionally, when the delivery system is centralized in the ball joint mechanism, the delivery system, the short station arm 150, and the axial member 160 are moving in the same direction. Additional details regarding potential embodiments may be found in FIGS. 28-34.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A delivery system for performing a minimally invasive procedure, the system comprising:
    one or more station legs configured to attach to an operating surface;
    a cross-beam connected to the one or more station legs and running from 0° to 45° relative to a top of the operating surface, wherein a distance between the operating surface and the cross-beam is adjustable;
    a first arm comprising a rail system, wherein the first arm is connected to the cross-beam;
    a second arm connected to the first arm, wherein the second arm is configured to slide, using the rail system, along at least a portion of the first arm's length; and
    an axial member connected to the second arm, the axial member comprising an axial joint,
    wherein the delivery system is configured to be advanced to an internal target site using the axial joint while maintaining a stationary trajectory in relation to the internal target site; and
    wherein the delivery system trajectory is modifiable at the target site.

2. The delivery system of claim 1, wherein the one or more station legs are vertically adjustable in relation to the operating surface.

3. The delivery system of claim 1, wherein the second arm and axial member are connected using a rotational joint, and wherein the axial member is configured to rotate using the rotational joint about a connection point.

4. The delivery system of claim 1, further comprising a support arm connected to the operating surface;
    wherein the support arm connects to the axial member; and
    wherein the support arm attaches to the operating surface via a rail system.

5. The delivery system of claim 1, wherein the first arm is configured to slide along a length of the cross-beam.

6. The delivery system of claim 1, wherein the one or more station legs attach to the operating surface via a rail system.

7. The delivery system of claim 1, wherein the second arm and axial member are connected using a rotational joint, and wherein the axial member is configured to rotate using the rotational joint about a connection point.

8. The delivery system of claim 1, further comprising a support arm connected to the operating surface.

9. The delivery system of claim 8, wherein the support arm connects to the axial member.

10. The delivery system of claim 8, wherein the support arm attaches to the operating surface via a rail system.

11. A delivery system for performing a minimally invasive procedure, the system comprising:
    one or more station legs configured to attach to an operating surface;
    a cross-beam connected to the one or more station legs and running from 0° to 45° relative to a top of the operating surface, wherein a distance between the operating surface and the cross-beam is adjustable;
    a first arm connected to the cross-beam;
    a second arm connected to the first arm using a rotational joint, wherein the second arm is configured to rotate using the rotational joint about a connection point; and
    an axial member connected to the second arm, the axial member comprising an axial joint,
    wherein the delivery system is configured to be advanced to an internal target site using the axial joint while maintaining a stationary trajectory in relation to the internal target site; and
    wherein the delivery system trajectory is modifiable at the target site.

12. The delivery system of claim 11, wherein the one or more station legs are vertically adjustable in relation to the operating surface.

13. The delivery system of claim 11, wherein the second arm and axial member are connected using a rotational joint, and wherein the axial member is configured to rotate using the rotational joint about a connection point.

14. The delivery system of claim 11, further comprising a support arm connected to the operating surface;
    wherein the support arm connects to the axial member; and
    wherein the support arm attaches to the operating surface via a rail system.

15. The delivery system of claim 11, wherein the first arm is configured to slide along a length of the cross-beam.

16. The delivery system of claim 11, wherein the one or more station legs attach to the operating surface via a rail system.

17. The delivery system of claim 11, wherein the second arm and axial member are connected using a rotational joint, and wherein the axial member is configured to rotate using the rotational joint about a connection point.

18. The delivery system of claim 11, further comprising a support arm connected to the operating surface.

19. The delivery system of claim 18, wherein the support arm connects to the axial member.

20. The delivery system of claim 18, wherein the support arm attaches to the operating surface via a rail system.

* * * * *